(12) United States Patent
Raymo et al.

(10) Patent No.: US 7,790,068 B2
(45) Date of Patent: Sep. 7, 2010

(54) PHOTOCHROMIC COMPOUNDS BASED ON RING OPENING AND CLOSING OF A {1,3}OXAZINE COMPOUND

(75) Inventors: Francisco M. Raymo, Coral Gable, FL (US); Massimiliano Tomasulo, Miami, FL (US)

(73) Assignee: The University of Miami, Miami, FL (US)

( * ) Notice: Subject to any disclaimer, the term of this patent is extended or adjusted under 35 U.S.C. 154(b) by 0 days.

(21) Appl. No.: 11/708,132

(22) Filed: Feb. 20, 2007

(65) Prior Publication Data

US 2007/0221889 A1   Sep. 27, 2007

Related U.S. Application Data

(60) Provisional application No. 60/774,190, filed on Feb. 17, 2006.

(51) Int. Cl.
*F21V 9/00* (2006.01)
*G02B 5/02* (2006.01)
*G02C 7/10* (2006.01)
*G02F 1/361* (2006.01)
*G03B 11/00* (2006.01)

(52) U.S. Cl. ............... 252/582; 252/586; 252/600; 359/321

(58) Field of Classification Search ............ 252/582, 252/586, 600; 359/321
See application file for complete search history.

(56) References Cited

U.S. PATENT DOCUMENTS

2007/0112103 A1*   5/2007   Zhou et al. ............. 524/90

OTHER PUBLICATIONS

Sackus, A.; Degutis, J.; Urbonavicius, A. Synthesis and investigation of 5a,6-dihydro-12H-indolo[2,1-☐☐b][1,3]benzoxazine derivatives Kaunas. Politekh. Inst., Kaunas, 233006, USSR, Khimiya Geterotsiklicheskikh Soedinenii (1989), (5), 672-6.*

Tomasulo, Massimiliano; Sortino, Salvatore; Raymo, Francisco M. A Fast and Stable Photochromic Switch Based on the Opening and Closing of an Oxazine Ring, Organic Letters (2005), 7(6), 1109-1112.*

A. Shachkus, S. Krikshtolaitite, and V. Martinaitis, Synthesis of [1,3] benzoxazino[2,3-k]- and [2,4] benzodiazepine[3,2-k]- carbazole derivatives, Chemistry of Heterocyclic Compounds, vol. 35, No. 6, 1999.*

Françisco M. Raymo and Silvia Giordani, All-optical processing with molecular switches, PNAS Apr. 16, 2002, vol. 99, No. 8, 4941-4944.*

Massimiliano Tomasulo and Françisco M. Raymo, Optical writing and reading with bilayer assemblies of photosensitive and fluorescent films, J. Mater. Chem., 2005, 15, 4354-4360.*

Massimiliano Tomasulo, Salvatore Sortino, and Francüisco M. Raymo, A Fast and Stable Photochromic Switch Based on the Opening and Closing of an Oxazine Ring, Organic Letters 2005 vol. 7, No. 6 1109-1112, 2005 American Chemical Society.*

* cited by examiner

*Primary Examiner*—Ling-Siu Choi
*Assistant Examiner*—Bijan Ahvazi
(74) *Attorney, Agent, or Firm*—Nixon & Vanderhye P.C.

(57) ABSTRACT

We have designed a molecular switch based on the photoinduced opening and thermal closing of a [1,3]oxazine ring. A substituted [1,3]oxazine compound described as having a general (i.e., unsubstituted) structure with fused indoline and benzooxazine fragments such that they share a common bond in the [1,3]oxazine compound: (i) the bond connecting positions 1 and 2 of the indoline fragment and (ii) the bond connecting positions 2 and 3 of the benzooxazine fragment. Irradiation by light of suitable wavelength and intensity of this photochromic compound induces cleavage of a [C—O] bond of the [1,3]oxazine ring to form a phenolate chromophore. The photogenerated (e.g., colored) isomer may revert thermally to the starting (e.g., colorless) oxazine. Alternatively, the switch may be between isomers of the compound that absorb at different wavelengths. Reversible coloration of silica or polymeric materials and switching optical signals may involve many cycles of interconversion between different colored states. A colorless/colored state may be maintained by constant irradiation or chemical trapping.

5 Claims, 14 Drawing Sheets

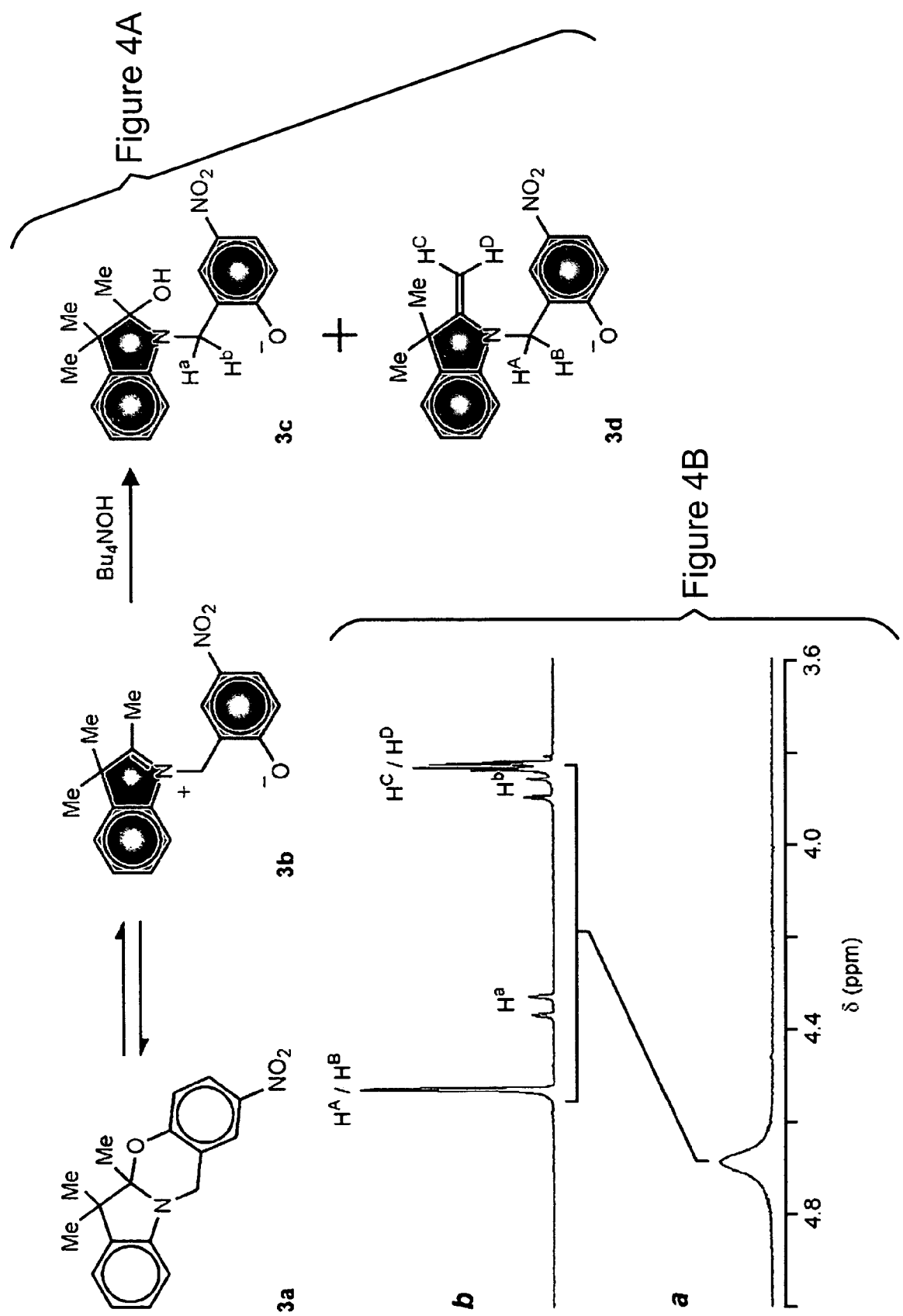

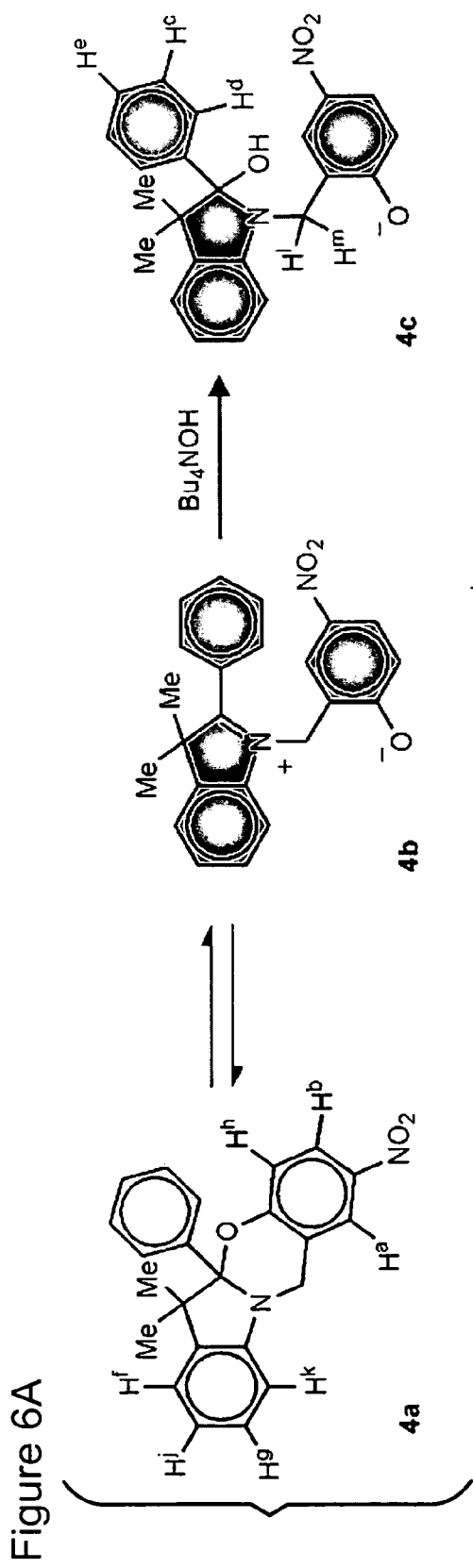
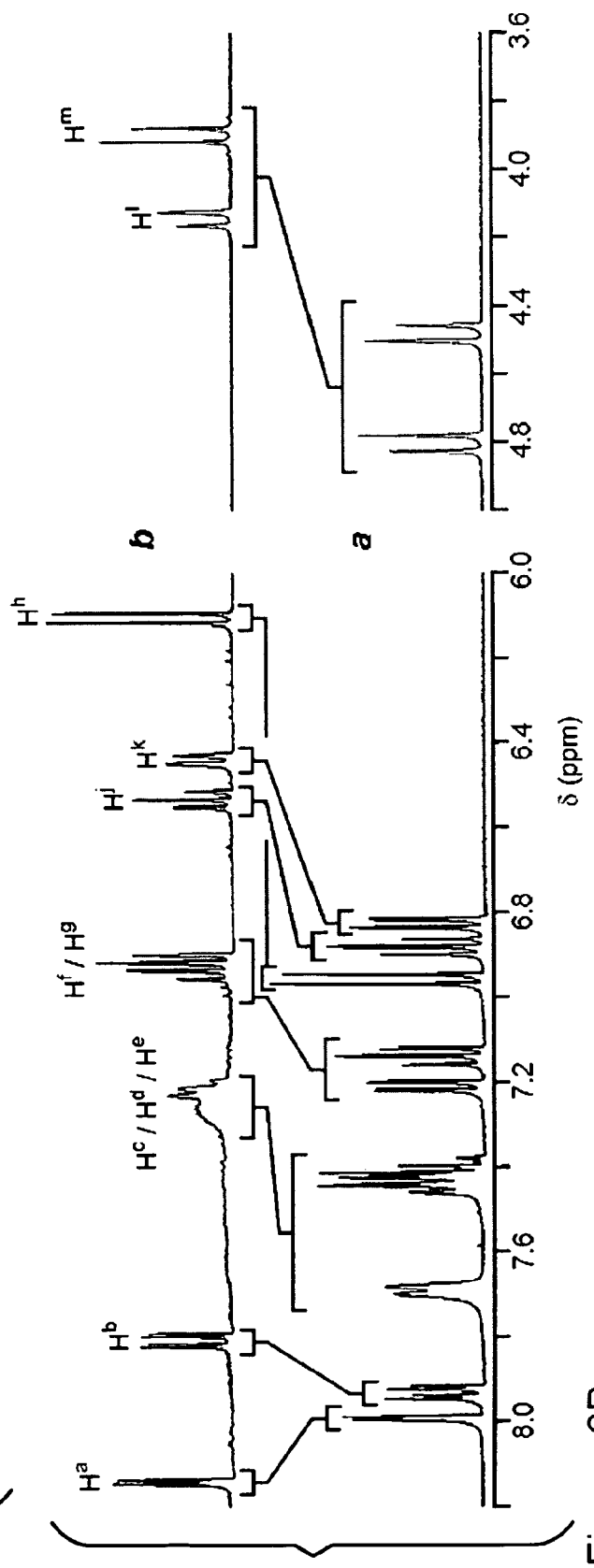
Figure 6A
Figure 6B

US 7,790,068 B2

PHOTOCHROMIC COMPOUNDS BASED ON RING OPENING AND CLOSING OF A {1,3}OXAZINE COMPOUND

CROSS-REFERENCE TO RELATED APPLICATIONS

This application claims priority benefit of provisional U.S. Application No. 60/774,190, filed Feb. 17, 2006.

FEDERALLY-SPONSORED RESEARCH OR DEVELOPMENT

The U.S. Government has certain rights in this invention as provided for by the terms of CHE-0237578 awarded by the National Science Foundation.

BACKGROUND OF THE INVENTION

This invention relates to substituted [1,3]oxazine compounds with a general (i.e., unsubstituted) structural formula described by fused indoline and benzooxazine fragments such that they are fused along the bond connecting positions 1 and 2 of the indoline fragment and the bond connecting positions 2 and 3 of the benzooxazine fragment. These products, as well as processes to make them or to use them, are provided.

Photochromic compounds change their color when illuminated. In most cases, a colorless compound switches to a colored compound upon illumination by light of suitable wavelength and intensity. The photogenerated species reverts to the starting species by either thermal means or further illumination. These reversible chemical transformations are accompanied by pronounced structural and electronic modifications, which often alter the ability of the photochromic compound to emit light. Under these conditions, the photo-induced and reversible interconversion of the colorless and colored states results in the modulation of the fluorescence intensity. Thus, this mechanism of light-induced transformation and reversion can be exploited to regulate the emissive behavior of collections of molecules in solution and even in solids. The investigation of these fascinating systems have led to new light-responsive materials for applications such as ophthalmic lenses for corrective or cosmetic purposes, optical filters to selectively transmit light, optical limiters to nonlinearly decrease their transmittance in response to increased incident light, photonic switches (including routers) to enable optical communication, public or personal displays of text or pictures, and silica or polymeric panes adapted for installation in "smart" windows of homes and buildings.

The term "photochromism" indicates a photoinduced change in color. Rather than the interconversion between two colored states, however, these transformations usually involve a transition from a colorless state to a colored state. Though less common, photoinduced transitions from colored to colorless forms are also possible. Indeed, the definitions "positive photochromism" and "negative photochromism" are often employed to distinguish coloration and decoloration processes, respectively. In any case, a photochromic transformation is always accompanied by profound absorbance changes in the visible region. In fact, visible absorption spectroscopy is the most convenient analytical method to study these processes.

Reversibility is an essential requirement for photochromic transformations. The photoinduced absorbance changes must be reversible by definition. In fact, photochromic compounds can be classified into two broad categories depending on the nature of the reverse process. Both classes share in common the ability to switch from one state to another when irradiated by light. Thermally stable photochromic compounds retain the photogenerated state even after turning off the light source, but return to the starting state after irradiation at a different wavelength. Thermally reversible photochromic compounds, instead, return to the starting state spontaneously when the irradiation is terminated.

Photochromic transformations are generally based on either unimolecular or bimolecular reactions. In most instances, unimolecular photochromic processes involve interconversion between two isomer forms. They can be based on light-induced ring opening/closing, cis/trans isomerizations, or intramolecular proton transfer. Bimolecular photochromic processes are less common. They rely on either the photoinduced cycloaddition of two identical reactants into a single product or on the photoinduced transfer of an electron from a donor to a complementary acceptor.

We have investigated a spiropyran as a photochromic compound, but it suffers at least two major limitations. Its thermal re-isomerization is relatively slow. Thus, restoration of the starting state is delayed by several minutes once the light is turned off and many applications require a quicker response. Furthermore, our spiropyran tolerates only a limited number of switching cycles.

Therefore, it is an objective of the invention to provide an improved class of photochromic compounds that undergo photoinducible [1,3]oxazine ring opening and revert by [1,3] oxazine ring closing. Irradiation of a compound triggers photo-induced cleavage of a [C—O] bond of the [1,3]oxazine ring to form a phenolate chromophore. The photogenerated (colored) isomer may revert thermally to the starting (colorless) isomer. Reversible coloration of transparent or translucent silica or polymeric materials and light-induced switching may involve multiple cycles of interconversion between different colored states. Our invention addresses the need for improved an photochromic compound with: (i) faster switching speed and (ii) better fatigue resistance than spiropyran compounds.

The present invention is directed to improved optical materials and systems for photochromic switching between two different optical states (e.g., a difference in light absorbance). Other advantages and improvements are described below or would be apparent from the disclosure herein.

SUMMARY OF THE INVENTION

An objective is providing a substituted [1,3]oxazine compound, wherein the unsubstituted [1,3]oxazine compound is described as having a structure with fused indoline and benzooxazine fragments such that they share a common bond in the [1,3]oxazine compound: (i) the bond connecting positions 1 and 2 of the indoline fragment and (ii) the bond connecting positions 2 and 3 of the benzooxazine fragment. Other than optional substitutions at one or more positions on the fused ring systems, there is a further substitution of an electron withdrawing group attached at any position of a phenyl ring of the system. It is preferred that the carbon atom between nitrogen and oxygen of the [1,3]oxazine ring be a tertiary carbon that is the position of one of the optional substitutions.

In one embodiment, the substituted [1,3]oxazine compound has Formula I. Selection of $R^1$, $R^4$, and $R^5$ can determine (i) the compound's responsiveness to light (e.g., the excitation wavelength and intensity that induces ring cleavage) and (ii) the absorbance wavelength of the phenolate derivative. Selection of $R^2$ and $R^3$ can affect the rates of isomerization and/or re-isomerization. In particular, colorless and colored states may be switched by irradiating the compound with visible light of suitable wavelength and intensity, and then removing the light source to allow thermal re-isomerization.

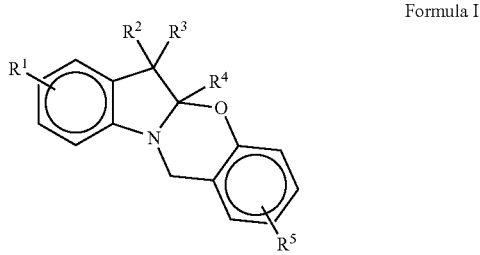

Formula I $R^1$ may be hydrogen, hydroxyl, C1-C4 alkyl, C5-C6 cycloalkyl, substituted C1-C4 alkyl, substituted C5-C6 cycloalkyl, C5-C6 aryl, substituted C5-C6 aryl, C5-C6 heterocycle, or substituted C5-C6 heterocycle. $R^1$ may be positioned at any position on a phenyl of the fused ring system, but the position opposite the attachment point of the nitrogen atom is preferred. $R^2$ and $R^3$ may be the same or different: hydrogen, hydroxyl, C1-C4 alkyl, C5-C6 cycloalkyl, substituted C1-C4 alkyl, substituted C5-C6 cycloalkyl, C5-C6 aryl, substituted C5-C6 aryl, C5-C6 heterocycle, or substituted C5-C6 heterocycle. $R^4$ may be hydrogen, hydroxyl, C1-C4 alkyl, C5-C6 cycloalkyl, substituted C1-C4 alkyl, substituted C5-C6 cycloalkyl, C5-C6 aryl, substituted C5-C6 aryl, C5-C6 heterocycle, or substituted C5-C6 heterocycle. $R^5$ may be a nitrogen-containing group or any other electron withdrawing substituent (e.g., cyanide and halides such as chloro, bromo, and fluoro); it may be positioned at any position on a phenyl of the fused ring system, but the position opposite the attachment point of the oxygen atom is preferred.

Also provided are processes for using and making the products. For example, [1,3]oxazine compounds may be synthesized by fusing indoline and benzooxazine fragments (e.g., N-alkylating 2-$R^4$-3,3'-$R^2$,$R^3$-6-$R^1$-3H-indole with 2-chloromethyl-4-$R^5$-phenol to produce an intermediate and then cyclizing the intermediate under basic conditions). Using such compounds by irradiating them with light (e.g., from 200 nm to 800 nm, 800 nm to 1300 nm, etc.) opens the [1,3]oxazine ring by cleaving a [C—O] bond to generate a phenolate chromophore that is able to absorb light, preferably visible. Reversion occurs by reformation of the [C—O] bond. The hemiaminal form may be trapped by using a nucleophile. Optical filters, optical limiters, ophthalmic lenses, photonic switches, or window panes that respond rapidly to a change in light and maintain this property through many cycles may be fabricated.

Further aspects of the invention will be apparent to a person skilled in the art from the following description of specific embodiments and the claims, and generalizations thereto.

BRIEF DESCRIPTION OF THE DRAWINGS

FIG. 4 shows (FIG. 4A) the compound OX1 and (FIG. 4B) its partial $^1$H-NMR spectra (400 MHz, CD$_3$CN, 10 mM) before (a) and after (b) the addition of Bu$_4$NOH (2 equiv.).

FIG. 6 shows (FIG. 6A) the compound OX2 and (FIG. 6B) its partial $^1$H-NMR spectra (400 MHz, CD$_3$CN, 10 mM) before (a) and after (b) the addition of Bu$_4$NOH (2 equiv.).

DETAILED DESCRIPTION OF SPECIFIC EMBODIMENTS

Figure 2:
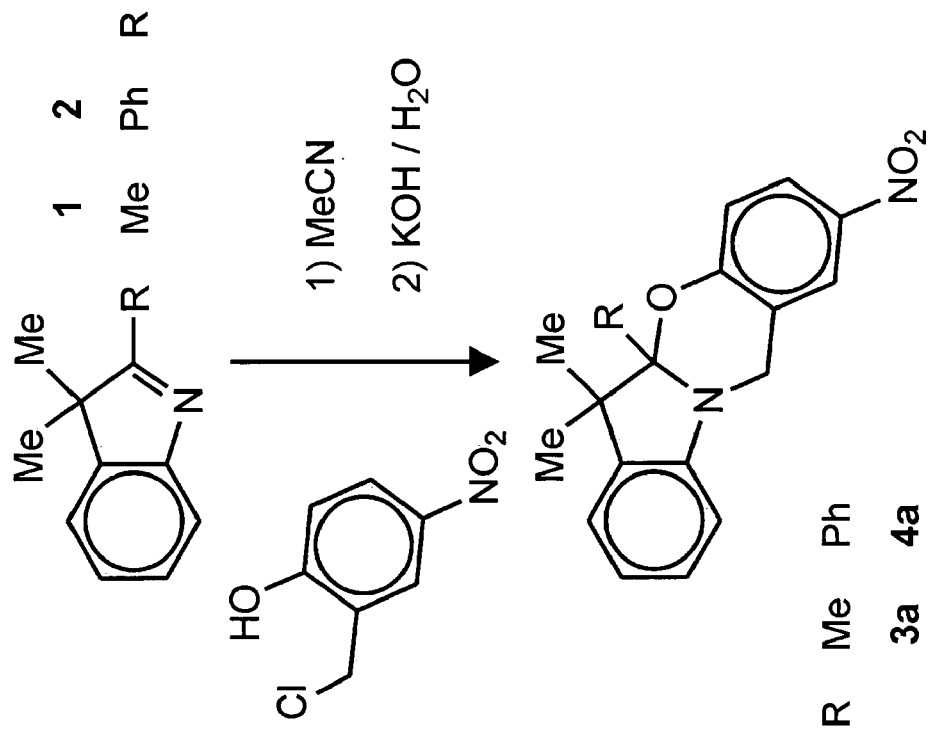
FIG. 2 is a schematic of the synthesis of [1,3]oxazine compounds OX1 and OX2.

The structural and electronic changes that accompany the light-induced transformation of photochromic compounds have suggested a wealth of applications over the past four decades. These compounds have emerged as convenient building blocks for constructing photoswitchable assemblies. In these systems, interconversion between the different states of a photochromic compound may modulate the optical properties of the overall assembly. The promise offered by photonic technology may be advanced by the novel photochromic compounds of the invention with the goal of developing innovative light-responsive materials for display, information processing, storage, therapy, and visualization.

Photochromic compounds change their structural and electronic properties in response to optical stimulation. The photogenerated state reverts to the starting state either thermally or after the application of a second optical stimulation differing in wavelength from the first. Thermally-reversible photochromes offer the opportunity to alter and reset the state of an output property (e.g., absorption or refractive index) by simply turning on and off a light source, since they do not retain the influence of the incident radiation. The ability to restore output level and the lack of memory effects are essential conditions for the implementation of combinational logic functions. As a result, these compounds have emerged as possible building blocks for the construction of molecular logic gates. Indeed, recent investigations have demonstrated that collections of photochromic compounds in solution or within rigid matrices can reproduce logic functions relying on the interplay of optical signals.

Photochromic compounds are the building blocks of light-responsive materials (e.g., ophthalmic lenses for corrective or cosmetic purposes, optical filters or limiters to modulate light signals, photonic switches to enable optical communication, public or personal displays of text or pictures, and silica or polymeric panes adapted for installation in "smart" windows of homes, offices, and vehicles). They generally require several minutes to switch from a colorless to a colored state and vice versa. These relatively slow processes limit the switching times of current photochromic materials, which need several minutes to adjust in response to changes in light intensity. Our compounds, instead, can switch between colorless and colored states in nanoseconds. Their rapid isomerization kinetics can, therefore, translate into an improvement of ten orders of magnitude in the switching times of photochromic materials.

Light-responsive public displays (e.g., billboards and stadium scoreboards) and personal displays (e.g., mounted on vertical or horizontal surfaces), filters and/or limiters in optical assemblies and systems, photonic switches for optical communication, ophthalmic lenses of contacts and glasses, and "smart" window panes adapted for installation in a home, office, or vehicle window may be fabricated using these photochromic compounds in optical materials. For example, the optical material may darken (i.e., absorb light) in response to irradiation by light of suitable wavelength and intensity.

Figure 1:
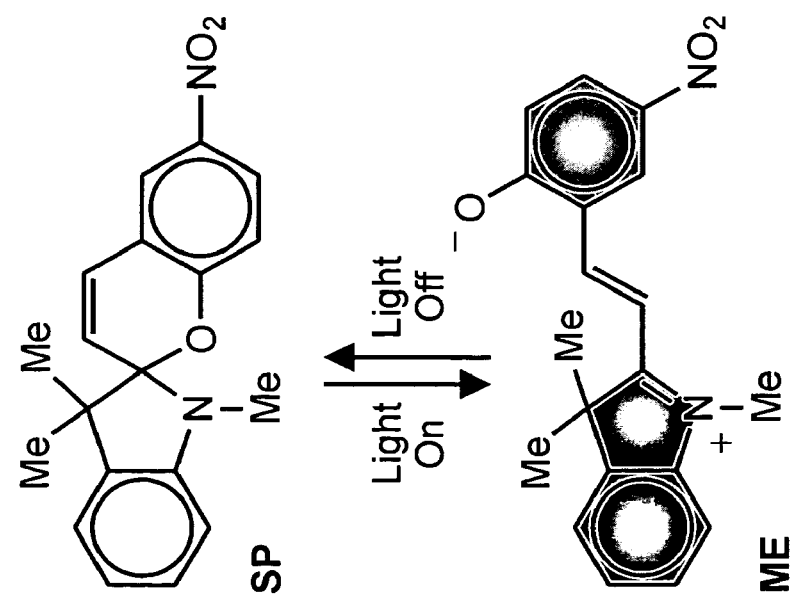
FIG. 1 is a schematic of the reversible interconversion between colorless spiropyran (SP) and colored merocyanine (ME) isomers.

The photoinduced isomerization of spiropyrans (e.g., SP in FIG. 1) involves two consecutive steps. Upon ultraviolet irradiation, the [C—O] bond at the spirocenter cleaves in picoseconds. Then, the adjacent [C═C] bond switches from a cis to a trans configuration in microseconds. The thermal transformation of the resulting merocyanine (e.g., ME in FIG. 1) back to the starting spiropyran is slowed significantly by a necessary trans→cis re-isomerization step. For example, ME switches back to SP in minutes with a rate constant of about $25 \times 10^{-4}$ s$^{-1}$ in MeCN at 25° C.

The present invention provides a substituted [1,3]oxazine compound, wherein the unsubstituted [1,3]oxazine compound is described as having a structure with fused indoline and benzooxazine fragments such that they share a common bond in the [1,3]oxazine compound: (i) the bond connecting positions 1 and 2 of the indoline fragment and (ii) the bond connecting positions 2 and 3 of the benzooxazine fragment. The two fused heterocycle fragments are constrained with respect to each other such that the dihedral angle formed between the axis of the $2p_z$ orbital on the indoline nitrogen atom and the adjacent $\sigma_{C-O}$ orbital is acute (e.g., 15° to 30°). Bulky substituents near the dihedral angle are avoided. Although substitutions at one or more positions of the fused ring systems (e.g., preferred are one, two, three, or four substitutions for a hydrogen of the unsubstituted [1,3]oxazine compound) may be optional, substitution of an electron-withdrawing substituent at any position of a phenyl ring of the fused ring system is mandatory.

It is preferred that one of the optional substitutions occurs at the carbon atom between nitrogen atom and oxygen atom of the [1,3]oxazine ring to provide a tertiary carbon. In such embodiments, this chiral carbon atom and the nitrogen atom are shared between the two fused heterocycle fragments of the [1,3]oxazine compound.

In one embodiment, the substituted [1,3]oxazine compound has Formula I. Cleavage of a [C—O] bond in the [1,3]oxazine ring produces a phenolate derivative, which preferably absorbs visible light. Selection of $R^1$, $R^4$, and $R^5$ can determine (i) the compound's responsiveness to light (e.g., the excitation wavelength and intensity that induces ring cleavage) and (ii) the absorbance wavelength of the phenolate derivative. Selection of $R^2$ and $R^3$ (e.g., methyl substituents) can affect the rates of isomerization and/or re-isomerization. In particular, colorless and colored states may be switched by irradiating the compound with visible light of suitable wavelength and intensity, and then removing the light source to allow thermal re-isomerization. A hemiaminal form may be trapped with a nucleophile that competes with the ring-closing reaction to form the hemiaminal.

Formula I

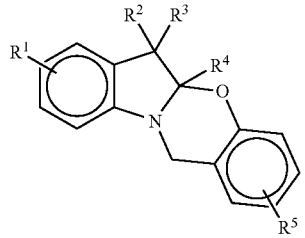

$R^1$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cyclo-alkyl, C5-C6 aryl (e.g., furyl, phenyl), substituted (e.g., halide, hydroxyl) C5-C6 aryl (e.g., halide, hydroxyl), C5-C6 heterocycle, or substituted (e.g., halide, hydroxyl) C5-C6 heterocycle. $R^1$ may be positioned at any position on a phenyl of the fused ring system, but the position opposite the attachment point of the nitrogen atom is preferred. $R^2$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl (e.g., halide, hydroxyl), C5-C6 heterocycle, or substituted (e.g., halide, hydroxyl) C5-C6 heterocycle, or fused ring systems (e.g., biphenyl). $R^3$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl (e.g., halide, hydroxyl), C5-C6 heterocycle, substituted (e.g., halide, hydroxyl) C5-C6 heterocycle, or fused ring systems (e.g., biphenyl). $R^4$ may be hydrogen, hydroxyl, C1-C4 alkyl (e.g., methyl, ethyl, propyl, butyl) or C5-C6 cycloalkyl, substituted (e.g., halide, hydroxyl) C1-C4 alkyl or C5-C6 cycloalkyl, C5-C6 aryl (e.g., furyl, phenyl), substituted (e.g., halide, hydroxyl) C5-C6 aryl (e.g., halide, hydroxyl), C5-C6 heterocycle, substituted (e.g., halide, hydroxyl) C5-C6 heterocycle, or fused ring systems (e.g., biphenyl). $R^5$ may be a nitrogen-containing group (e.g., nitroso, nitro, azo dyes) or any other electron withdrawing substituent (e.g., cyano, halides). $R^5$ may be positioned at any position on a phenyl of the fused ring system, but the position opposite the attachment point of the oxygen atom is preferred. The relative orientation of the fused, substantially planar heterocycles constrains the dihedral angle between the axis of the $2p_z$ orbital on the indoline nitrogen atom and that of the adjacent $\sigma_{C-O}$ orbital. Bulky substituents at $R^2$, $R^3$, and $R^4$ near the dihedral angle are avoided.

The compound may be switched by irradiating with a light source (e.g., dye or gas laser, lamp, light emitting diode). Switches results in an isomeric shift between the compound and its phenolate derivative, and their absorbance of visible light shifts from colorless (starting compound) to colored (phenolate derivative) by this isomerization. Depending on the excitation wavelength of the compound, the switch results in the maximum absorbance wavelength to shift by a positive or negative difference of at least 50 nm, at least 100 nm, at least 150 nm, at least 200 nm, at least 250 nm, or at least 300 nm.

The light may have a wavelength from 200 nm to 1300 nm, 400 nm or more, at least 600 nm or more, at least 800 nm or more, 800 nm or less, 1000 nm or less, 1300 nm or less, or any range therebetween. The light source may be a laser diode (e.g., from 200 nm to 800 nm) or a light emitting diode (LED) (e.g., from 800 nm to 1300 nm). Illumination may be provided by constant or pulsed light. Preferably, the intensity of the light is slow and the time of illumination is short.

A photoinducible optical state may be maintained by constant illumination or by chemical trapping (e.g., nucleophile) of an isomer in the form of the hemiaminal. Most of the compounds in a composition may switch between isomeric states within 5 ns or less, 10 ns or less, 50 ns or less, or 250 ns or less. Compounds remain able to photoactivate and revert over greater than 1000 excitation cycles, greater than 3000 excitation cycles, or greater than 5000 excitation cycles.

The compound may be incorporated in silica, a liquid crystal, or a polymeric material or in one or more sheets of such material as a laminate. The material may be a flexible or rigid solid, preferably it is transparent or translucent. Alternatively, the compound may be dissolved in a liquid (e.g., solution or gel) and then encapsulated in a solid material (e.g., applied in a thin film, cast or molded as a sheet, segregated in beads or laminated structures). The material may be amorphous (e.g., glass) or crystalline (e.g., quartz). Examples of polymeric materials include polycarbonate, polymethylmethacrylate, and polystyrene.

If incorporated in a solid material or encapsulated within a solid material, the material is preferably at least opaque to the wavelength of light that induces switching in the compound and does not attenuate the intensity of light such that switching is not efficient. In particular, the compounds may be dissolved in an organic solvent and its function is not oxygen sensitive.

Specific embodiments of the invention are the OX1 and OX2 compounds (FIG. 2). In analogy to SP, ultraviolet irradiation of OX1 or OX2 induces the cleavage of a [C—O] bond, involving the tertiary carbon of the indoline fragment, with the formation of a p-nitrophenolate chromophore. The resulting indolium lacks the central double bond of ME. Thus, the rate of the thermal transformation of indolium back to oxazine should not be limited by the relatively slow trans→cis re-isomerization associated with ME.

We have synthesized OX1 and OX2 in two steps (FIG. 2) with an overall yield of 58%. Specifically, the N-alkylation of either 2-methyl-3,3'-dimethyl-3H-indole (1) or 2-phenyl-3,3'-dimethyl-3H-indole (2) with 2-chloromethyl-4-nitrophenol, and then the cyclization under basic conditions resulted in OX1 or OX2. In general, [1,3]oxazine photochromic compounds may be synthesized by fusing indoline and benzooxazine fragments starting from $2\text{-}R^4\text{-}3,3'\text{-}R^2,R^3\text{-}3H$-indoles and 2-chloromethyl-4-nitrophenol, wherein $R^1$ is hydrogen and $R^5$ is nitro. For OX1 and OX2, $R^1$ is hydrogen, $R^2$ and $R^3$ are methyl, and $R^5$ is nitro OX1 and OX2 differ in the substitution attached to the tetrahedral carbon atom shared by the indoline and benzooxazine fragments. The relative orientation of these two fused heterocycles constrains the dihedral angle between the axis of the $2p_z$ orbital on the indoline nitrogen atom and that of the adjacent $\sigma_{O-C}$ orbital to values comparable to those (15° to 30°) of nitrospiropyrans. Thus, this particular geometry is expected to favor electronic mixing between the two orbitals and facilitate cleavage of the [C—O] bond in the excited state, as observed for nitrospiropyrans. It follows that ultraviolet irradiation of either OX1 or OX2 should open the [1,3]oxazine ring to generate a 4-nitrophenolate chromophore able to absorb violet light.

Figure 3A:
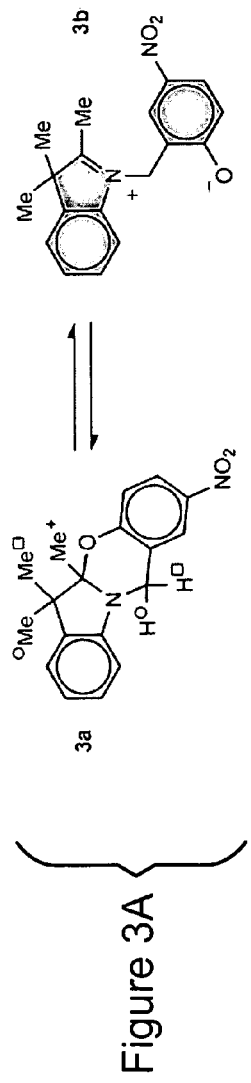
FIG. 3 shows (FIG. 3A) the compound OX1 and (FIG. 3B) its partial $^1$H-NMR spectra (500 MHz, CD$_3$CN, 5 mM) at 2° C. (a), 10° C. (b), 20° C. (c), 40° C. (d), 50° C. (e), and 63° C. (f).
Figure 3B:
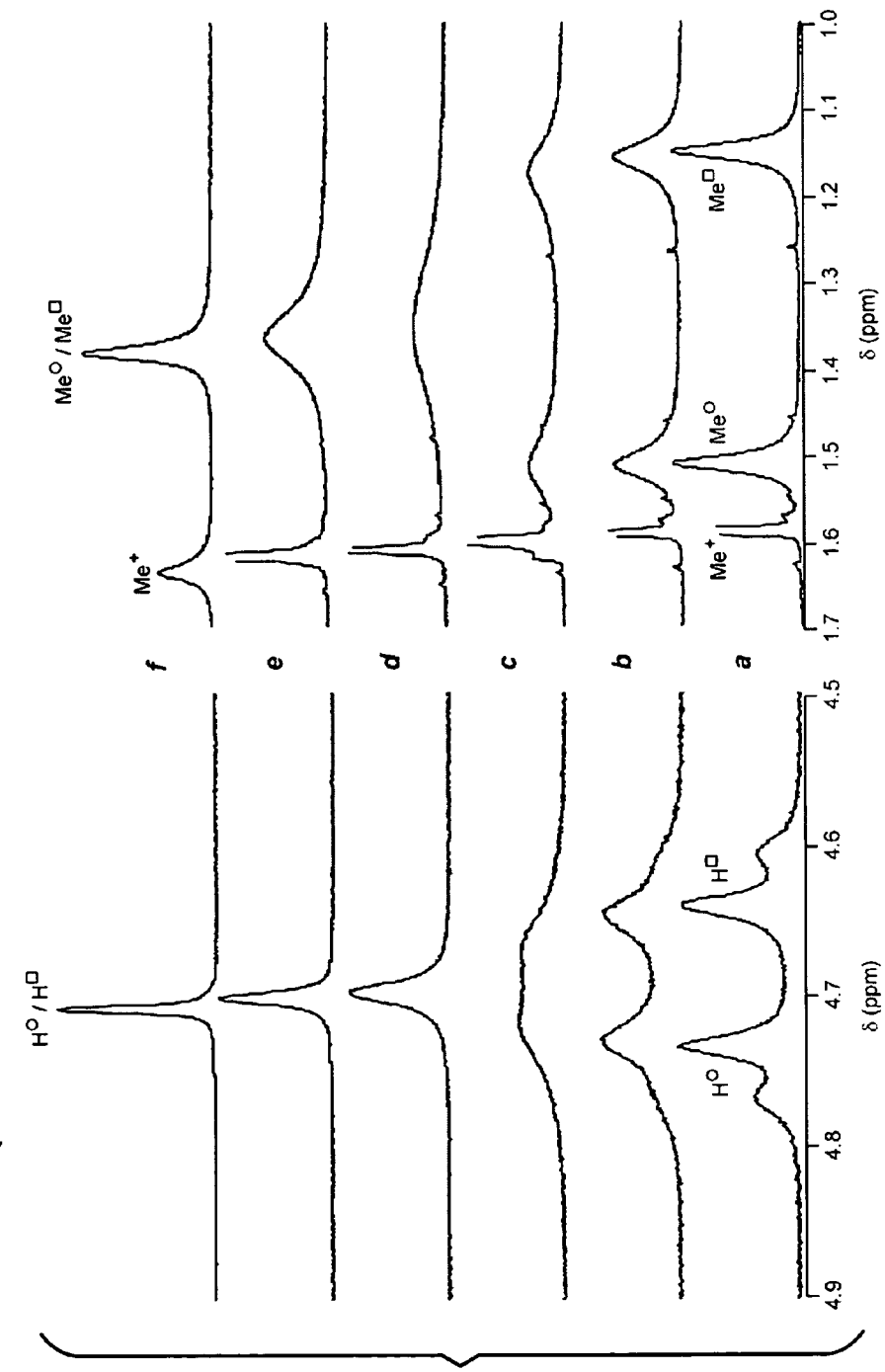

The chiral center at the junction of the two fused heterocycles in OX1 and OX2 imposes two distinct environments on the pair of indoline methyl groups and the pair of oxazine methylene protons. Consistently, the $^1$H NMR spectra of both compounds reveal pairs of singlets for the methyl protons and AB systems for the methylene protons, when recorded in acetonitrile-d3 at ambient temperature. For example, the two singlets for the methyl protons (Me° and Me$^\square$) of OX1 (FIG. 3A) appear at 1.15 and 1.51 ppm in the $^1$H-NMR spectrum (a in FIG. 3B) recorded at 2° C. The AB system for the methylene protons (H° and H$^\square$) is instead centered at 4.69 ppm. Upon warming the solution, the two singlets broaden (b to f in FIG. 3B) and eventually coalesce into a single peak. Similarly, the two doublets within the AB system broaden and coalesce into a single peak. These changes are a result of the interconversion between the two enantiomers of OX1 on the $^1$H NMR time scale. This degenerate site exchange process demands the thermal cleavage of the [C—O] bond at the junction of the two heterocycles with the formation of the ring-opened intermediate (FIG. 3A).

The addition of Bu$_4$NOH to a solution of OX1 (FIG. 4A) has similar effects on the $^1$H NMR and mass spectra. Once again, peaks for the corresponding hemiaminal (FIG. 4B) can be clearly observed. The methyl group in position 2 of the indolium fragment, however, is relatively acidic. Thus, the nucleophilic attack of the hydroxide anion to the indolium cation competes with its deprotonation and another compound (FIG. 4A) is formed in parallel to the hemiaminal. Consistently, the broad resonance for the pair of diastereotopic methylene protons of OX1 (a in FIG. 4B) is replaced by an AB system for $H^a$ and $H^b$ of the hemiaminal and a singlet for H$^a$ and H$^b$ of the another compound (b in FIG. 4B). In addition, an AB system for the olefinic protons H$^c$ and H$^d$ of the another compound can also be observed. From the integrals of these resonances, the ratio between hemiaminal and the compound is estimated to be 34:66.

The kinetic parameters (Table 1) associated with the ring-opening process can be extracted from the analysis of the temperature dependence of the line widths associated with the singlets for Me° and Me□ in the slow-exchange regime. A similar analysis of OX2 (FIG. 5A) can be extended to the $^1$H NMR spectra (FIG. 5B), which reveal essentially the same behavior.

the formation of the hemiaminal is further confirmed by the presence of a peak at an m/z of 390 in the fast atom bombardment mass spectrum.

The two chromophoric fragments of OX1 and OX2 are isolated electronically. As a result, their absorption spectra (a in FIGS. 7A and 8A) resemble the sum of those (b and c in FIGS. 7A and 8A) of model indolines (5 and 6 in Table 2) and 4-nitroanisole (7 in Table 2). The most significant difference is a shift to longer wavelengths for the absorption associated with the 4-nitrophenyl chromophore. This band is centered at 307 nm in the spectrum of 7 (Table 2), but at 318 and 316 nm in those of OX1 and OX2, respectively.

TABLE 1

Kinetic parameters associated with the thermal ring opening of OX1 and OX2 at 25° C.$^a$

| Solvent | Compound | k (s$^{-1}$) | ΔG$^‡$ (kcal mol$^{-1}$) | ΔH$^‡$ (kcal mol$^{-1}$) | −ΔS$^‡$ (kcal mol$^{-1}$ K$^{-1}$) |
|---|---|---|---|---|---|
| Acetonitrile-d3 | OX1 | 199 ± 7 | 14.31 ± 0.02 | 13.5 ± 0.2 | 0.003 ± 0.001 |
| | OX2 | 0.4 ± 0.1 | 17.99 ± 0.18 | 17.4 ± 0.3 | 0.002 ± 0.001 |
| Toluene-d8$^b$ | OX1 | 0.081 ± 0.036 | 19.00 ± 0.29 | 19.8 ± 2.0 | −0.003 ± 0.006 |

$^a$The rate constant (k), free energy (ΔG$^‡$), enthalpy (ΔH$^‡$) and entropy (ΔS$^‡$) of activation were determined by variable-temperature $^1$H NMR spectroscopy.
$^b$In toluene-d8, the line widths of the singlets associated with the pair of methyl protons of OX2 remain approximately constant in the examined temperature range (2° C.-90° C.). As a result, the kinetic parameters for the ring opening of this compound could not be determined.

A comparison of the rate constants (k in Table 1) determined for the thermal ring opening of OX1 and OX2 in acetonitrile-d3 reveals that the group on the chiral center at the junction of the two heterocycles has a pronounced influence on the kinetics of this process. Indeed, a transition from the methyl group of OX1 to the phenyl ring of OX2 translates into a decrease in k from about 199 to 0.4 s$^{-1}$. This change corresponds to an increase in free energy barrier (ΔG$^‡$ in Table 1) of about 3.7 kcal mol$^{-1}$. Interestingly, the enthalpic term (ΔH$^‡$ in Table 1) dominates ΔG$^‡$, while the entropic contribution (TΔS$^‡$) at 25° C. is less than 1 kcal mol$^{-1}$ for both compounds. In toluene-d8, TΔS$^‡$ remains negligible, but ΔH$^‡$ increases by about 4.7 kcal mol$^{-1}$ for OX1. Consistently with the solvent-induced enhancement in ΔH$^‡$, the $^1$H NMR spectrum of OX1 does not change significantly with temperature in toluene-d8. Two well-defined singlets for the methyl protons of OX2 can clearly be observed even at 90° C., in agreement with the slow ring-opening kinetics.

Figures 5A, 5B:
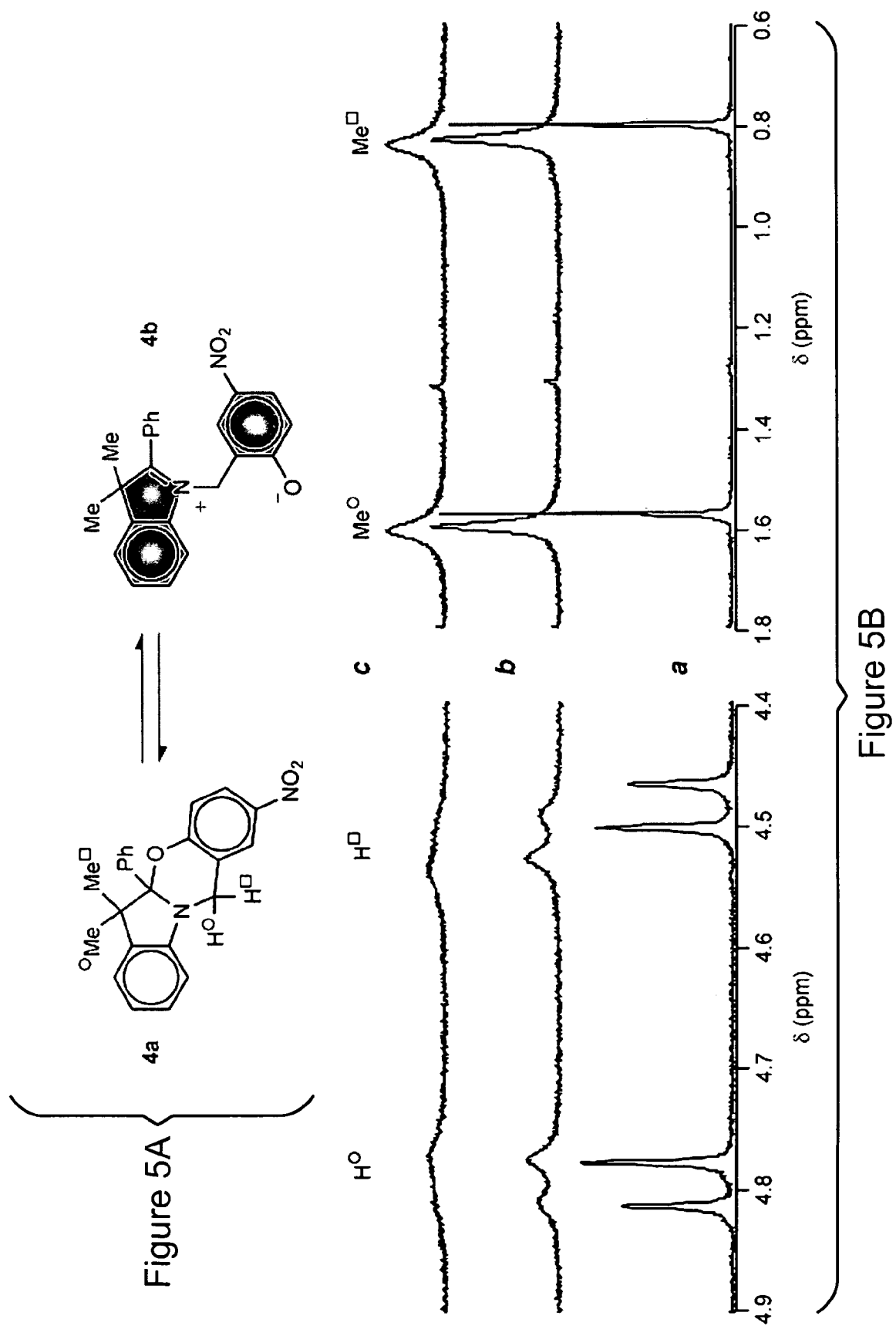
FIG. 5 shows (FIG. 5A) the compound OX2 and (FIG. 5B) its partial $^1$H-NMR spectra (500 MHz, CD$_3$CN, 5 mM) at 30° C. (a), 60° C. (b), and 70° C. (c).

The ring-opened intermediates revert to the corresponding oxazines OX1 and OX2 after the intramolecular attack of the 4-nitrophenolate anion to the adjacent indolium cation (cf. FIGS. 3A and 5A). Nucleophiles able to compete intermolecularly with the ring-closing step can therefore "trap" these short-lived intermediates. For example, the addition of two equivalents of Bu$_4$NOH to a solution of OX2 results in the quantitative formation of the hemiaminal (FIG. 6A).

In agreement with the formation of the hemiaminal, the $^1$H-NMR spectrum of oxazine (a in FIG. 6B) changes dramatically after the addition of Bu$_4$NOH (b in FIG. 6B). In particular, the chemical shift of the proton H$^a$ increases by 0.15 ppm with the transformation of oxazine into the hemiaminal. The signals of the other aromatic protons (H$^b$—H$^h$), instead, move in the opposite direction. The largest change is observed for the resonances associated with the proton H$^h$, whose chemical shift decreases by 0.85 ppm. Furthermore, the AB system associated with the diastereo-topic pair of methylene protons H$^l$ and H$^m$ is maintained, confirming the presence of a chiral center also in the hemiaminal. In addition,

TABLE 2

Absorption wavelengths (λ$_{max}$) and molar extinction coefficients (ε) of the oxazines OX1 and OX2 and of the model compounds 5-8 in MeCN at 25° C.$^a$

| Compound | λ$_{max}$ (nm) | ε (mM$^{-1}$cm$^{-1}$) |
|---|---|---|
| OX1 | 318 | 10.0 ± 0.5 |
| OX2 | 316 | 11.0 ± 0.6 |
| 5 | 283 | 2.2 ± 0.1 |
| 6 | 281 | 3.9 ± 0.2 |
| 7 | 307 | 11.1 ± 0.6 |
| 8 | 426 | 32.5 ± 0.9 |

$^a$Structures of 5-8 are shown below. λ$_{max}$ and ε of the phenolate 8 were determined by recording the absorption spectrum of the corresponding phenol in the presence of Bu$_4$NOH (4 equiv.).

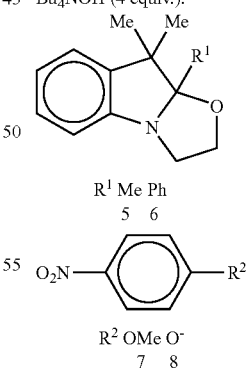

R$^1$ Me Ph
     5  6

R$^2$ OMe O$^-$
     7  8

Figure 7A:
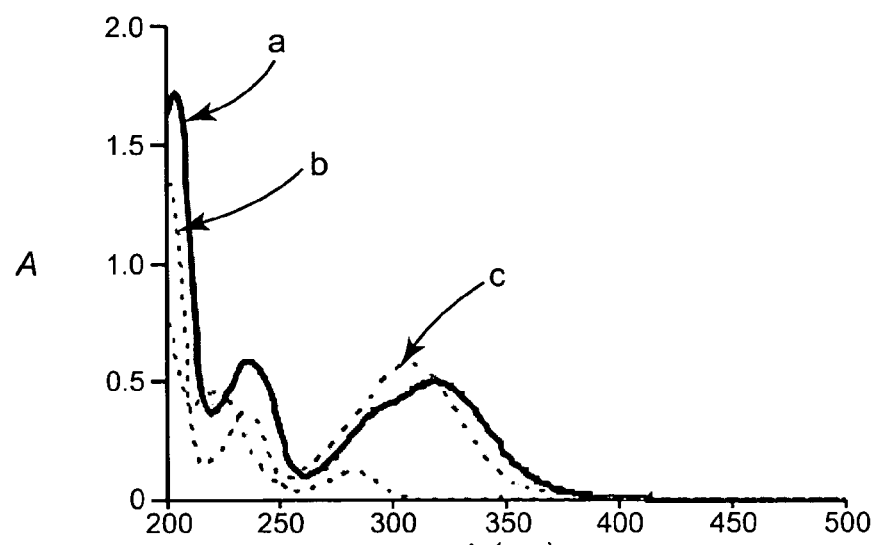
FIG. 7 shows steady-state absorption spectra (0.1 mM, MeCN, 25° C.) of (FIG. 7A) OX1 (a), 5 (b) and 7 (c) as well as (FIG. 7B) OX1 after the addition of Bu$_4$NOH (1 equiv.) (d) and 8 (e).
Figure 7B:
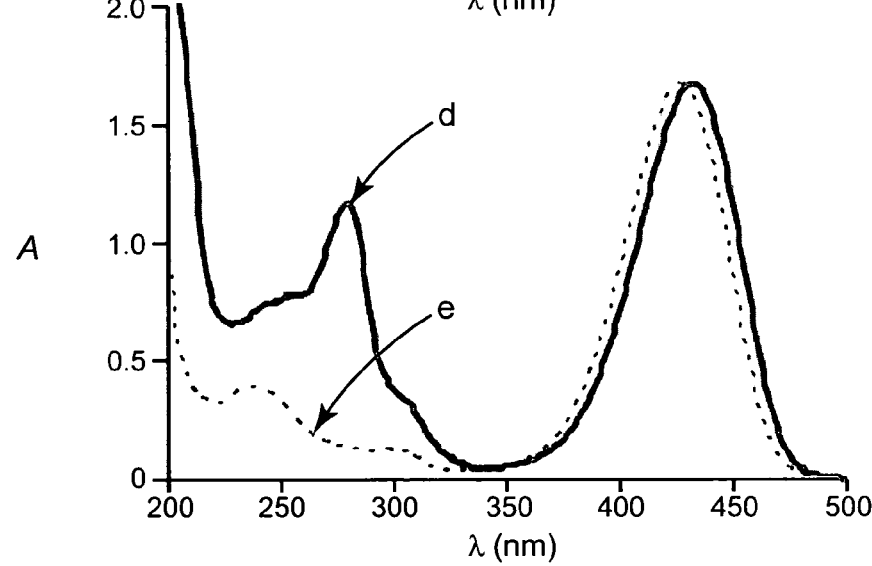
Figure 8A:
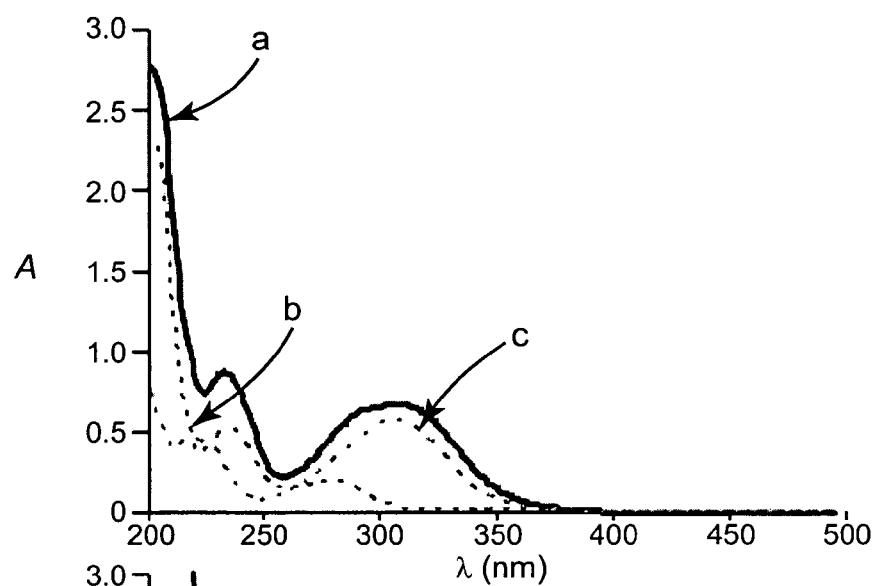
FIG. 8 shows steady-state absorption spectra (0.1 mM, MeCN, 25° C.) of (FIG. 8A) OX2 (a), 6 (b) and 7 (c) as well as (FIG. 8B) OX2 after the addition of Bu$_4$NOH (100 equiv.) (d) and 8 (e).
Figure 8B:
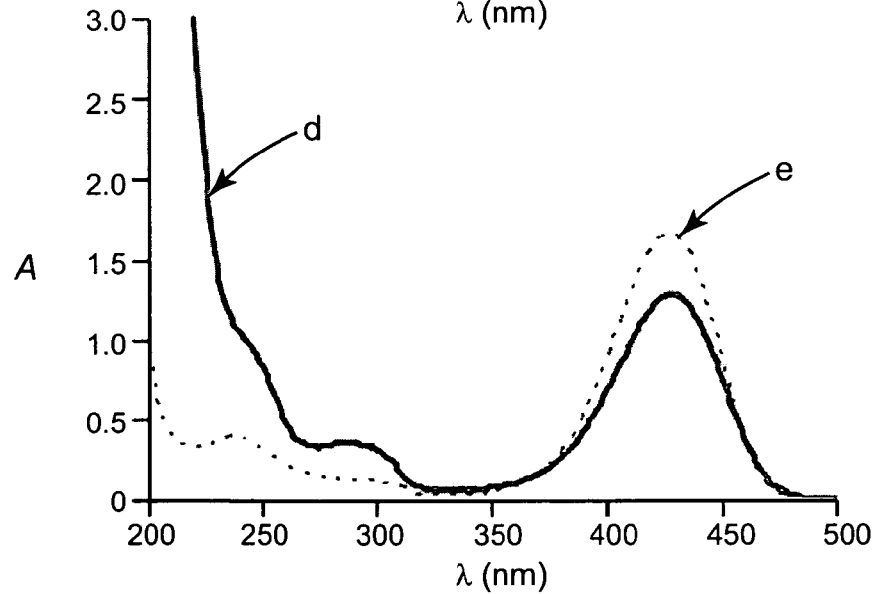

The spectra of OX1 and OX2 (a in FIGS. 7A and 8A) do not show bands in the wavelength range expected for a 4-nitrophenolate chromophore (e in FIGS. 7B and 8B). Thus, the stationary concentrations of the ring-opened isomers of OX1 and OX2 are below the detection limit in both cases, under these experimental conditions (MeCN, 25° C.). After the addition of Bu$_4$NOH to solutions of OX1 and OX2, however, a band at about 430 nm appears in the spectra of both species (d in FIGS. 7B and 8B). This band resembles the absorption (e in FIGS. 7B and 8B) of the model phenolate (Table 2) and can be assigned to the ring-opened products detected by $^1$H NMR spectroscopy (see FIGS. 4B and 6B).

Figure 9A:
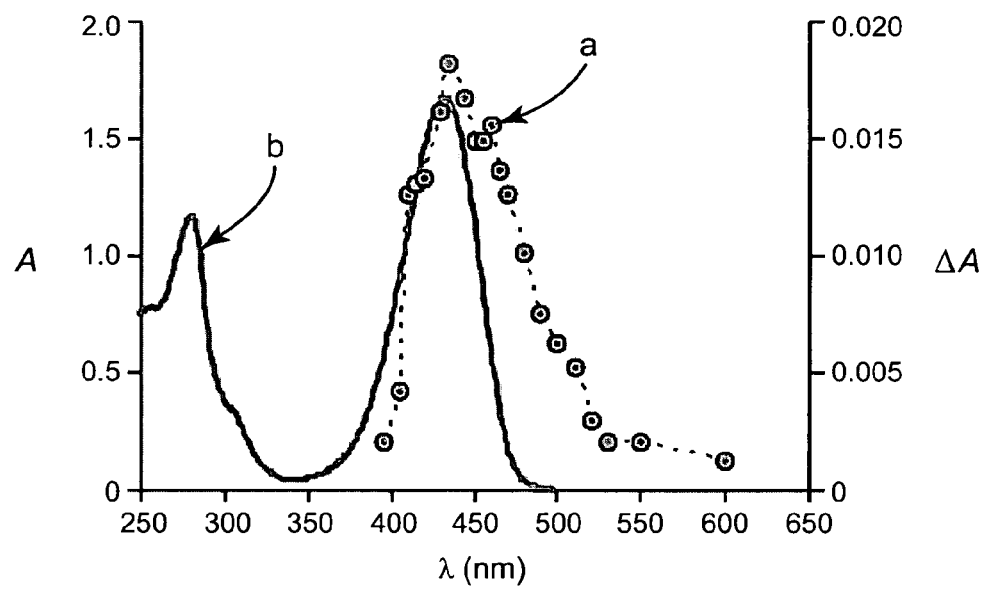
FIG. 9A shows a transient absorption spectrum of (a) OX1 recorded 30 ns after the laser pulse (355 nm, 6 ns, 8 mJ, 0.1 mM, MeCN, 22° C.) and a steady-state absorption spectrum (b) OX1 and 1 equiv. Bu$_4$NOH (0.1 mM, MeCN, 25° C.).
Figure 10A:
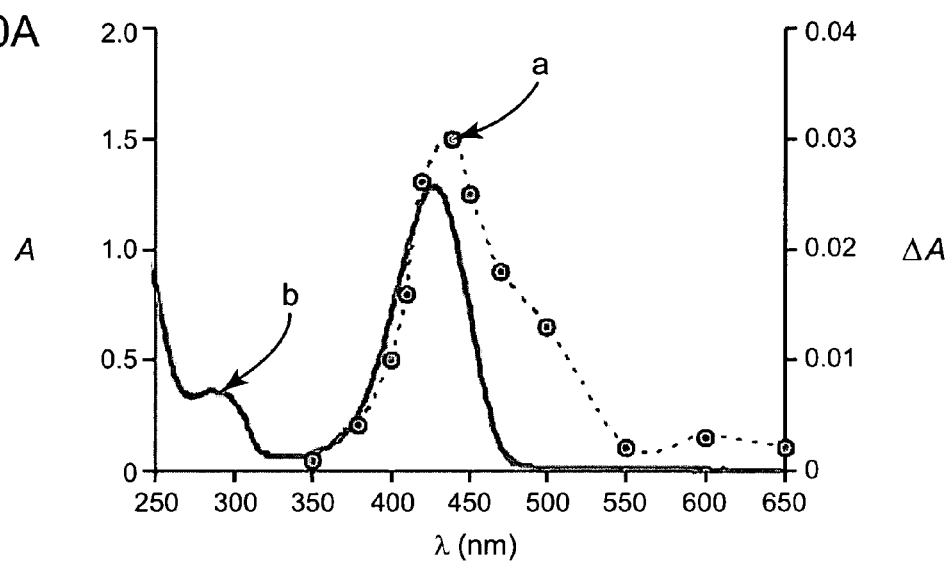
FIG. 10A shows a transient absorption spectrum (a) of OX2 recorded 30 ns after the laser pulse (355 nm, 6 ns, 8 mJ, 0.1 mM, MeCN, 22° C.) and a steady-state absorption spectrum (b) of OX2 and 100 equiv. Bu$_4$NOH (0.1 mM, MeCN, 25° C.).

Transient absorption spectra, recorded 30 ns after laser excitation, of aerated MeCN solutions of OX1 and OX2 show bands centered at about 440 nm (a in FIGS. 9A and 10A). In both instances, the transient bands resemble the steady-state ones (b in FIGS. 9A and 10A) and, therefore, can be assigned to ground-state absorptions of the 4-nitrophenolate chromophores. In agreement with this assignment, singlet-oxygen measurements for OX2 and control experiments with 7 confirm that the transient absorptions are not associated with a triplet-triplet transitions. Indeed, the quantum yield of singlet oxygen is less than 0.02 and the transient spectrum of 7 does not reveal any detectable absorption in the nanosecond domain.

Figure 9B:
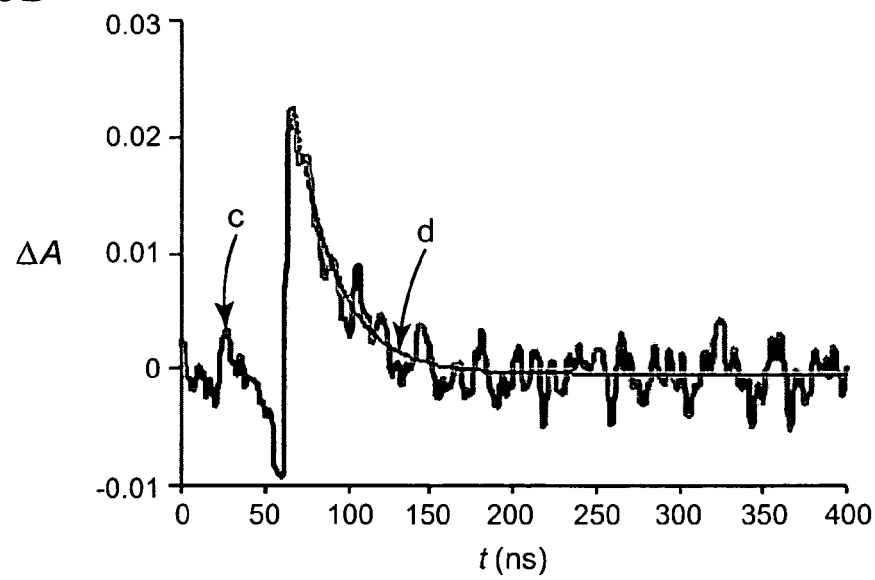
FIG. 9B shows the evolution of the absorbance at 440 nm (c) upon laser excitation of OX1 and the corresponding mono-exponential curve fitting (d).
Figure 10B:
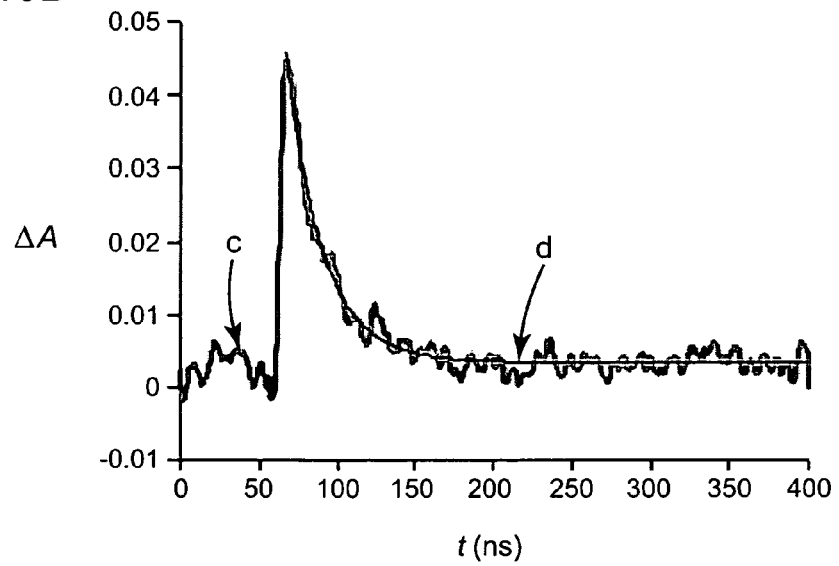
FIG. 10B shows the evolution of the absorbance at 440 nm (c) upon laser excitation of OX2 and the corresponding mono-exponential curve fitting (d).

The kinetic traces monitored at 440 nm (c in FIGS. 9B and 10B) indicate that the ring-opened isomers are formed within the excitation pulse (about 6 ns). The corresponding quantum yields can be estimated to be 0.03 and 0.1 for OX1 and OX2, respectively. In both instances, the absorbance decays monoexponentially to zero (d in FIGS. 9B and 10B) with a first-order rate constant of about $4\times10^7$ s$^{-1}$, as the ring-opened isomers revert thermally to OX1 and OX2.

Figure 11A:
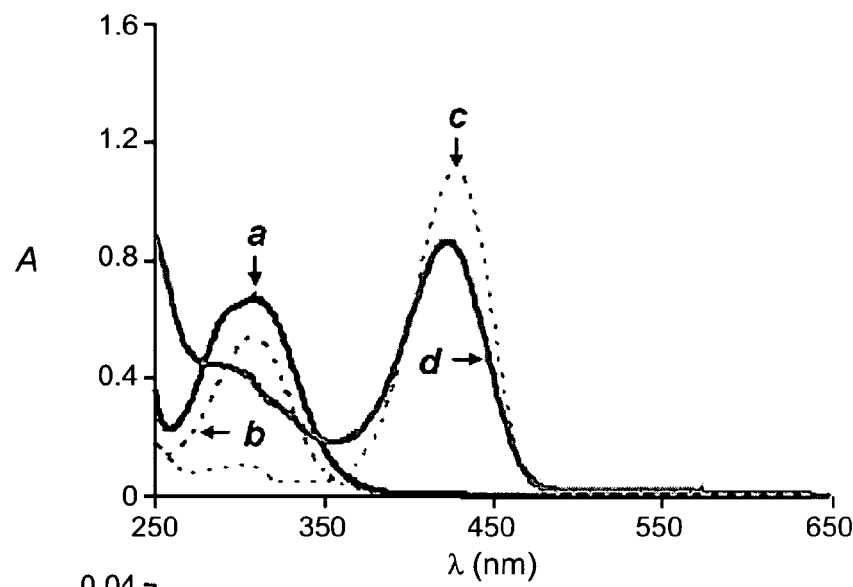
FIG. 11A shows steady-state absorption spectra (0.1 mM, MeCN, 20° C.) of OX2 (a), p-nitroanisole (b), potassium p-nitrophenolate (c), OX2 after the addition of Bu$_4$NOH (10 equiv.) and continuous irradiation (365 nm, 400 µW cm$^{-2}$) for 10 min (d).
Figure 12A:
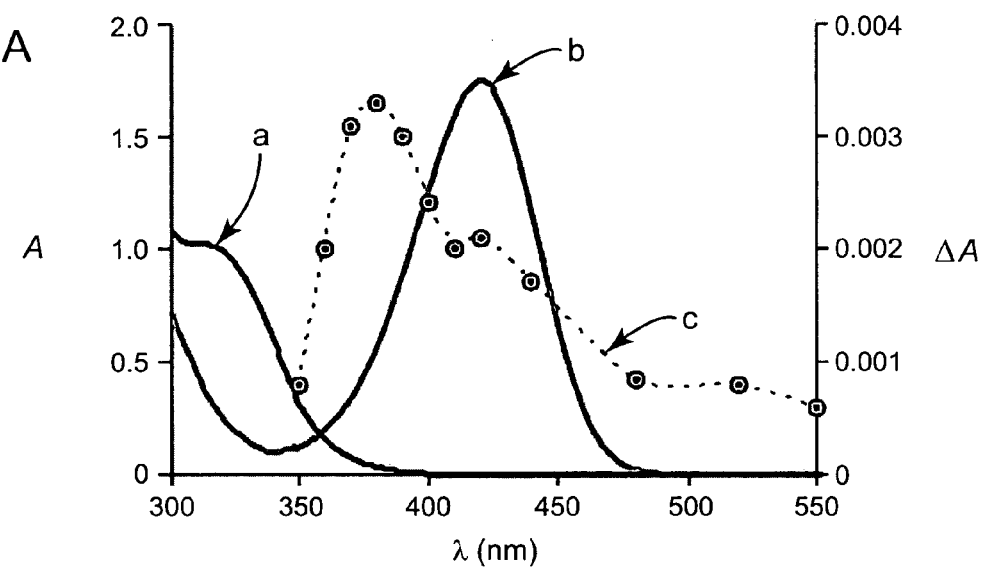
FIG. 12A shows steady-state absorption spectra (5%, PMMA, 25° C.) of OX1 without (a) and with (b) Bu$_4$NOH (7 equiv.) and transient absorption spectra of OX1 recorded 1 µs (c) after the laser pulse (355 nm, 6 ns, 12 mJ, 5%, PMMA, 22° C.).

The interconversion of the two enantiomers of oxazine demands the thermal opening of the oxazine ring with formation of indolium. Nonetheless, the stationary concentration of indolium is negligible and the steady-state absorption spectrum (a in FIGS. 11A and 12A) reveals only a band at 308 nm for the p-nitrophenoxy chromophore of OX2. Indeed, this absorption resembles the one observed for p-nitroanisole (b in FIGS. 11A and 12A), under identical experimental conditions. The characteristic band at 429 nm (c in FIGS. 11A and 12A) expected for the p-nitrophenolate component of indolium cannot, instead, be detected (a in FIGS. 11A and 12A). After the addition of Bu$_4$NOH and continuous irradiation of OX2, however, an intense absorption (d in FIG. 11A) for a p-nitrophenolate chromophore appears in the spectrum. Thus, the excitation of OX2 encourages the formation of indolium, which is "trapped" in the form of a hemiaminal (FIG. 6A) after attachment of the nucleophilic hydroxide anion to the electrophilic carbon of the indolium cation. Consistently, the fast atom bombardment mass spectrum recorded at this point shows a peak at a m/z of 390 for the hemiaminal.

Figure 11B:
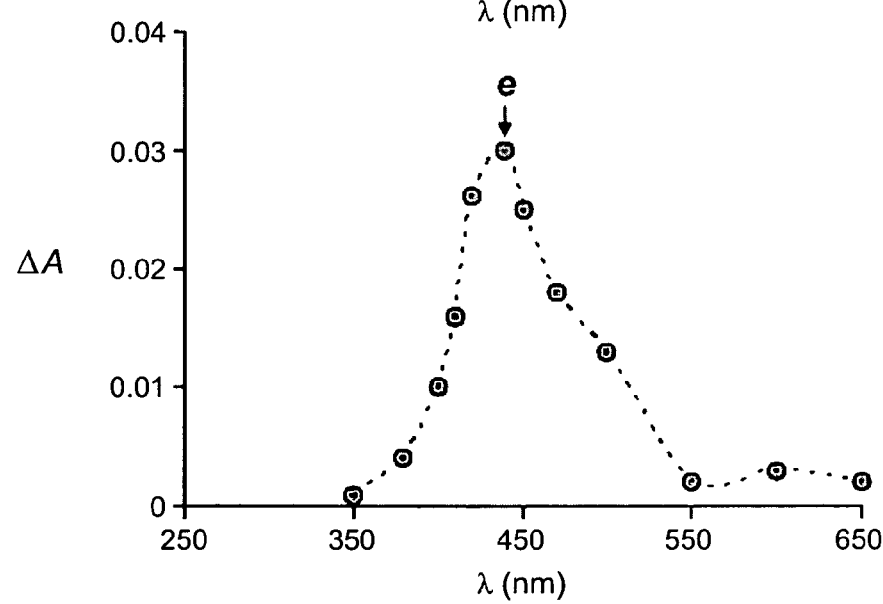
FIG. 11B shows the transient absorption spectrum (0.1 mM, MeCN, 22° C.) of OX2 (e) recorded 30 ns after a laser pulse (355 nm, 6 ns, 8 mJ).

Laser flash photolysis measurements confirm the photoinduced opening of the oxazine ring with the formation of indolium. Indeed, the transient absorption spectrum of OX2 (e in FIG. 11B), recorded 30 ns after laser excitation, shows a band at 440 nm, which can be assigned to a p-nitrophenolate chromophore (c to d in FIG. 11A). Consistent with this assignment, control experiments with p-nitroanisole exclude a possible association of this transient absorption with the triplet state of the p-nitrophenoxy fragment of oxazine. In fact, no transient absorptions are observed for p-nitroanisole, under identical experimental conditions. Furthermore, the quantum yield of singlet oxygen is less than 0.02, when the photoinduced conversion of oxazine into indolium is performed in air-saturated MeCN.

Figure 12B:
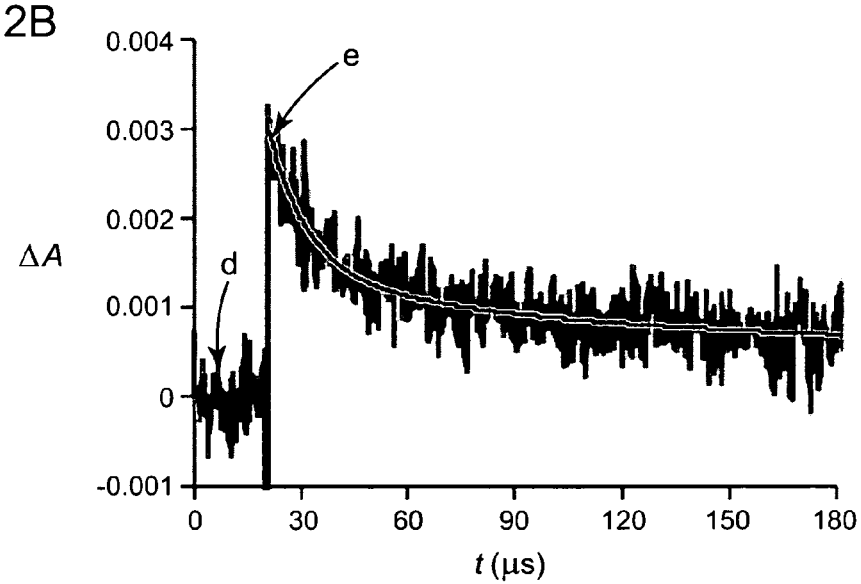
FIG. 12B shows the evolution of the absorbance at 380 nm (d) upon laser excitation of OX1 (355 nm, 6 ns, 12 mJ, 5%, PMMA, 22° C.) and the corresponding mono-exponential curve fitting (e).
Figure 13A:
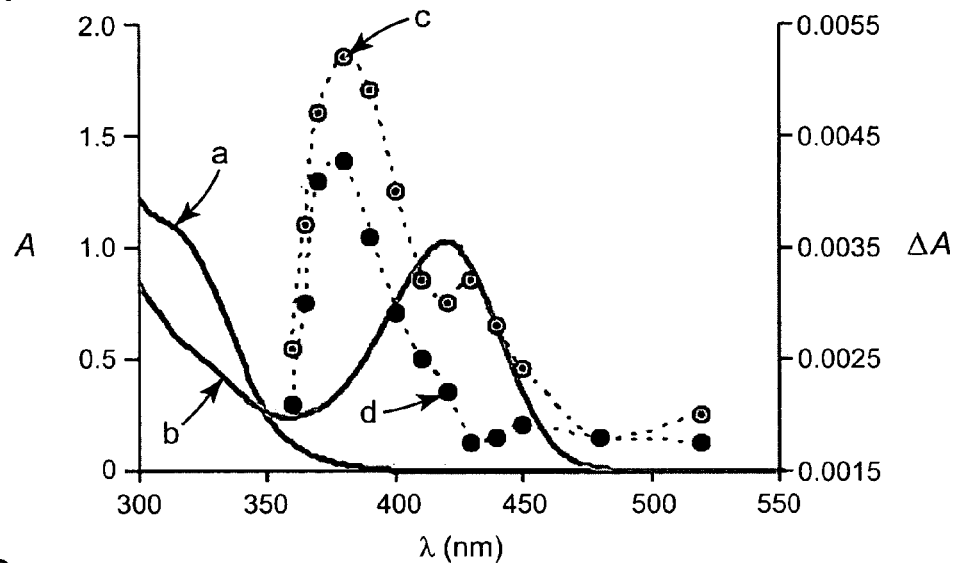
FIG. 13A shows steady-state absorption spectra (5%, PMMA, 25° C.) of OX2 without (a) and with (b) Bu$_4$NOH (7 equiv.) and transient absorption spectra of OX2 recorded 1 µs (c) or 80 µs (d) after the laser pulse (355 nm, 6 ns, 12 mJ, 5%, PMMA, 22° C.).
Figure 13B:
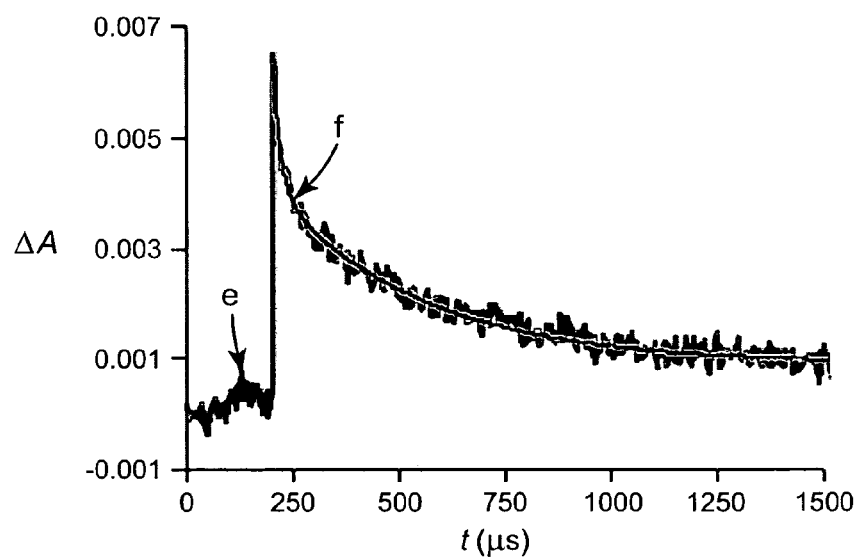
FIG. 13B shows the evolution of the absorbance at 380 nm (e) upon laser excitation of OX2 (355 nm, 6 ns, 12 mJ, 5%, PMMA, 22° C.) and the corresponding bi-exponential curve fitting (f).
Figure 14:
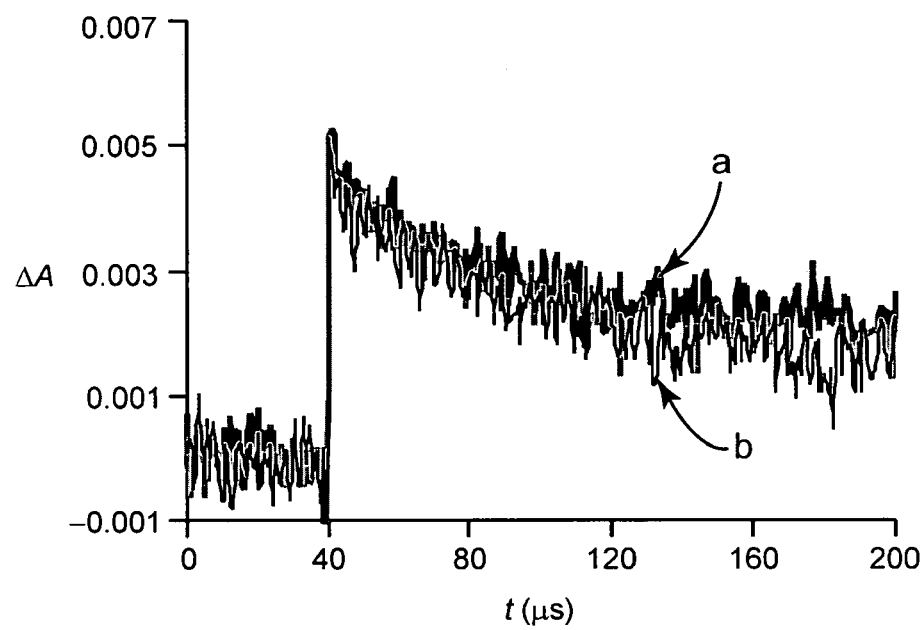
FIG. 14 shows the absorbance at 380 nm upon laser excitation of OX2 (355 nm, 6 ns, 12 mJ, 5%, PMMA, 22° C.) before (a) and after (b) 1000 excitation cycles.

Steady-state absorption spectra (a in FIGS. 12A and 13A) of polymethylmethacrylate (PMMA) films doped with OX1 or OX2 are essentially identical to those recorded in MeCN (see a in FIGS. 7A and 8A). Once again, the stationary concentrations of the ring-opened isomers are negligible and the absorption bands of their 4-nitrophenolate chromophores cannot be detected. In the presence of Bu$_4$NOH, however, the characteristic absorptions of hemiaminal forms at about 430 nm can be observed also in PMMA (b in FIGS. 12A and 13A). Similar bands are evident in the transient absorption spectra of OX1 and OX2 (c in FIGS. 12A and 13A) recorded 1 µs after laser excitation. These absorptions can be assigned to the photogenerated ring-opened isomers and are relatively short lived. After 80 µs, for example, the band at 430 nm can no longer be observed in the transient spectrum of OX2 (d in FIG. 13A). In addition to this absorption band, a second and more intense band at 380 nm (c in FIGS. 12-13) is evident in the transient spectra of both compounds. This absorption is relatively long lived and can still be observed after the complete decay of the band at 430 nm (d in FIG. 13A). The corresponding kinetic traces (d in FIG. 12B and e in FIG. 13B) show bi-exponential decay with rate constants of $1\times10^4$ and $1\times10^5$ s$^{-1}$ for OX1 and of $3\times10^3$ and $5\times10^4$ s$^{-1}$ for OX2. Both trends parallel the behavior of nitrospiropyrans in polymer matrices. Indeed, the thermal decoloration of nitrospiropyrans also follows bi-exponential kinetics under these experimental conditions. The aggregation of their photogenerated isomers into long-lived supramolecular assemblies is believed to be responsible for this behavior. Presumably, similar processes govern the spectral evolution of OX1 and OX2 in PMMA. In any case, the absorbance associated with the photogenerated species of both systems can be modulated reversibly with millisecond switching speeds. Once again, both photochromic switches are remarkably stable and remain essentially unaffected after thousands of excitation cycles. As an example, FIG. 14 illustrates kinetic traces recorded at 380 nm for OX2 before and after 1000 switching cycles. The profiles are virtually indistinguishable indicating that the photochromic switch is, indeed, extremely stable.

Figure 15:
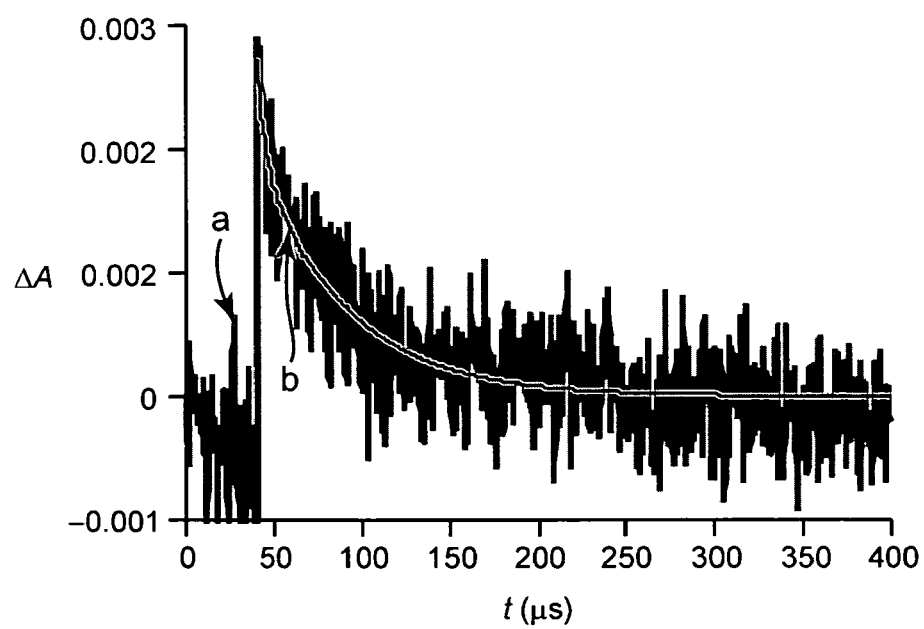
FIG. 15 shows evolution of the absorbance at 430 nm (a) upon laser excitation of OX2 (355 nm, 6 ns, 12 mJ, 5%, PMMA, 22° C.) and the corresponding bi-exponential curve fitting (b).

The evolution of the absorbance for OX1 (d to e in FIG. 12B) and OX2 (FIG. 15) indicates that the formation of indolium occurs within the laser pulse of about 6 ns. The quantum yield for the photoinduced conversion of OX2 into its indolium isomer is about 0.1. A kinetic analysis of the absorbance decay at 440 nm shows that the photogenerated indolium isomer reverts thermally to OX2 with a first-order rate constant of $(46\pm1)\times10^6$ s$^{-1}$. Therefore, the starting state is restored within about 50 ns.

Furthermore, the reversible interconversion between OX1 and OX2 and their indolium isomers is not accompanied by photodegradation, even in air-saturated solutions. Indeed, the transient absorption and steady-state spectra recorded before and after more than 3000 excitation cycles, in the presence of molecular oxygen, are virtually identical. Thus, substantially all of the [1,3]oxazine compound is recovered intact even after thousands of cycles. The remarkable photochemical stability of the [1,3]oxazine compounds agrees with their inability to sensitize efficiently the formation of singlet oxygen, which is responsible in part for the degradation of spiropyrans.

Figure 16:
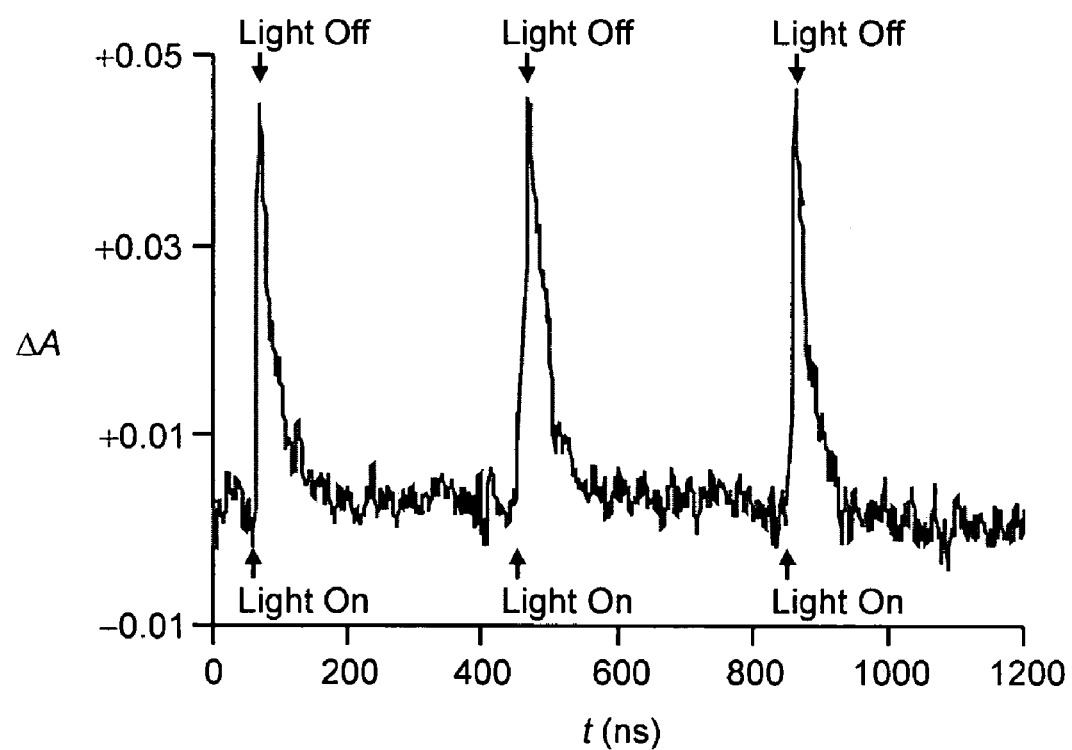
FIG. 16 shows the absorbance of indolium at 440 nm during three consecutive switching cycles of OX2 (0.1 mM, MeCN, 22° C.) performed by laser excitation (355 nm, 6 ns, 8 mJ).

The absorbances of the [1,3]oxazine compound and its phenolate derivative (see FIG. 16) can be altered and reset with nanosecond switching speeds by turning a light source on and off. The short time scales of these processes correspond to an improvement of ten orders of magnitude over any of our earlier all-optical processing schemes. The elimination of the sluggish trans→cis step, limiting the thermal re-isomerization of spiropyrans, has translated into this dramatic decrease in switching times. In addition, this structural modification has conferred remarkable stability on the photoresponsive molecular skeleton. The photoinduced and reversible interconversion between the [1,3]oxazine compound and its phenolate derivative can be achieved with nanosecond switching speeds. Furthermore, the significant changes in dipole moment and molecular polarizability accompanying the photoisomerization can, in principle, be exploited to photoregulate a diversity of material properties with unprecedented switching speeds. Thus, our molecular design for the realization of fast and stable photochromic compounds can evolve into the development of a new family of photoresponsive materials.

We have identified an innovative structural design to develop photochromic compounds with improved switching times and fatigue resistance. It is based on the fusion of indoline and benzooxazine fragments into a single molecular skeleton as shown below. The [1,3]oxazine ring in the compound (A) opens upon illumination. The cleavage of a [C—O] bond responsible for [1,3]ring opening is extremely fast and produces a phenolate derivative (B) with a switching time of less than a nanosecond. The photogenerated isomer also reverts thermally to the starting compound in nanoseconds. Thus, this particular molecular design offers the opportunity to switch between a colorless (A) and a colored (B) state in nanoseconds by simply turning on and off a visible light source. Furthermore, the process is not accompanied by photodegradation, even in the presence of molecular oxygen. Our photochromic compounds survive thousands of switching cycles without decomposing. In addition, our structural design tolerates a variety of substituents ($R^1$, $R^2$, $R^3$, $R^4$, $R^5$, or any combination thereof) on the indoline and benzooxazine fragments. These groups can be manipulated to regulate the excitation wavelength of A and the color of B, offering access to a new family of photochromic compounds with unprecedented switching speeds and stability.

uncorrected. Fast atom bombardment mass spectra (FABMS) were recorded with a VG Mass Lab Trio-2 spectrometer in a 3-nitrobenzyl alcohol matrix.

Nuclear magnetic resonance (NMR) spectra were recorded with a Bruker Avance 400 or a Bruker Avance 500 spectrometer. Steady-state absorption spectra were recorded with a Varian Cary 100 Bio spectrometer, either in aerated MeCN using quartz cells with a path length of 0.5 cm or in poly (methyl methacylate) (PMMA) matrices. The polymer films were prepared by spin-coating aliquots of $CH_2Cl_2$ solutions of PMMA (160 mg $mL^{-1}$) and either OX1 or OX2 (8 mg $mL^{-1}$) with and without $Bu_4NOH$ (7 equiv.) on glass plates at 429 rpm for 9 s. The thickness of the resulting films were about 6 μm and were measured with a digital micrometer. Transient absorption spectra were recorded with a commercial laser flash photolysis apparatus either in aerated MeCN, using quartz cells with a path length of 1.0 cm, or in PMMA matrices. The excitation source was a Nd:YAG laser (355 nm, 6 ns, 8 or 12 mJ). The quantum yield (Φ) for the photoinduced ring opening of OX1 and OX2 was determined with eq. 1, using an optically matched MeCN solution of benzophenone as standard. The quantum yield ($Φ_{BE}$) for the intersystem crossing of benzophenone is unity, and the molar extinction coefficient ($ε_{BE}$) for its triplet absorption at 520 nm is 6.5 $mM^{-1}$ $cm^{-1}$. The molar extinction coefficient of the ring-opened isomers at 440 nM was estimated to be about 22 $mM^{-1}$ $cm^1$. The terms in χ and $χ_{BE}$ are the slopes of the linear portions of plots of the photoinduced absorbance changes, measured at the end of the pulse, for the ring-opened isomer and the benzophenone triplet, respectively, against the energy of the laser pulse. Samples were irradiated continuously with

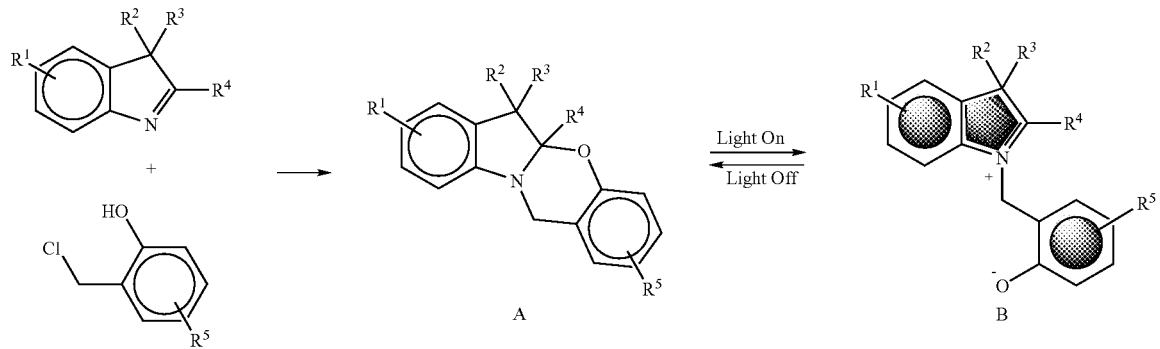

Materials & Methods

Chemicals were purchased from commercial sources and used as received with the exception of MeCN and $CH_2Cl_2$, which were distilled over $CaH_2$. 2-Methyl-3,3'-dimethyl-3H-indole (1) was purchased from a commercial source.

All reactions were monitored by thin layer chromatography, using aluminum sheets coated with silica (60, $F_{254}$). High-performance liquid chromatography (HPLC) was performed with analytical (column dimensions=4.6×250 mm, flow rate=1.0 mL $min^{-1}$, injection volume=10 μL, sample concentration=0.1 mM) and semi-preparative (column dimensions=21.4×250 mm, flow rate=10 mL $min^{-1}$, injection volume=10 mL, sample concentration=0.1 mM). The retention time (RT) and the peak asymmetry (PA) were determined at a wavelength of 254 nm. The average purity parameter (APP) was calculated for the peak heart in the wavelength range 215 nm to 700 nm. Melting points (mp) were determined with an Electrothermal Mel-Temp apparatus and are a Mineralight UVGL-25 lamp (365 nm, 10 min) when necessary. The output power (400 μW $cm^{-2}$) was determined with a Newport 1815-C meter.

2-Phenyl-3,3'-dimethyl-3H-indole (2). A mixture of phenylhydrazine (1.1 mL, 11 mmol), i-propylphenylketone (1.5 mL, 10 mmol) and p-toluenesulfonic acid (0.11 g, 0.6 mmol) was heated under reflux for 7 h. After cooling down to ambient temperature, the mixture was diluted with a saturated aqueous solution of $NaHCO_3$ (10 mL) and extracted with $CHCl_3$ (4×10 mL). The organic phase was dried ($MgSO_4$) and the solvent was evaporated under reduced pressure. The residue was dissolved in absolute EtOH (35 mL) and, after the addition of $ZnCl_2$ (14 g, 0.1 mol), was heated under reflux for 24 h. After cooling down to ambient temperature, the mixture was diluted with a saturated aqueous solution of $NaHCO_3$ (40 mL) and extracted with $Et_2O$ (3×10 mL). The organic phase was dried ($MgSO_4$) and the solvent was evaporated under reduced pressure. The residue was purified by column chromatography [SiO$_2$:CH$_2$Cl$_2$/heptane (4:1)] to afford the product (1.86 g, 84%) as an orange liquid. FABMS: m/z=222 [M]$^+$; $^1$H-NMR (500 MHz, CDCl$_3$): δ 1.55 (6H, s), 7.30 (1H, d, 8 Hz), 7.34-7.40 (2H, m), 7.47-7.53 (3H, m), 7.72 (1H, d, 8 Hz), 8.14-8.20 (2H, m); $^{13}$C-NMR (100 MHz, CDCl$_3$): δ 24.7, 53.5, 120.7, 120.9, 126.0, 127.7, 128.3, 128.4, 128.5, 130.6, 132.9, 147.4, 183.3.

2-Nitro-5a,6,6-trimethyl-5a,6-dihydro-12H-indolo[2,1-b][1,3]benzooxazine (OX1). A solution of 1 (291 µL, 1.8 mmol) and 2-chloromethyl-4-nitrophenol (162 mg, 0.9 mmol) in MeCN (5 mL) was stirred for 50 min at ambient temperature under N$_2$. Then, the mixture was stored in a refrigerator for 12 h. The resulting precipitate was filtered and dissolved in H$_2$O (40 mL). After the addition of aqueous KOH (0.05 M, 5 mL), the solution was extracted with Et$_2$O (3×20 mL). The organic layer was dried (MgSO$_4$) and filtered, and the solvent was distilled off under reduced pressure to give OX1 (94 mg, 0.3 mmol) as a white solid. The mother liquor of the initial filtration was concentrated under reduced pressure, and the residue was purified by column chromatography [SiO$_2$/CH$_2$Cl$_2$→CH$_2$Cl$_2$/MeCO$_2$Et (10:1)] to afford an additional amount of OX1 (60 mg, 0.2 mmol). The overall yield of OX1 was 58%. HPLC [analytical, MeCN/H$_2$O (80:20)]: RT=4.5 min, PA=1.6, APP=236.7±1.0 nm; mp=180° C.; FABMS: m/z=311 [M+H]$^+$; $^1$H-NMR (500 MHz, CDCl$_3$): δ 1.17 (3H, s), 1.52 (3H, s), 1.57 (1H, d, 11 Hz), 4.63 (1H, d, 11 Hz), 6.73 (1H, d, 8 Hz), 6.86-6.94 (2H, m), 7.16-7.19 (3H, s), 4.60 (2H, m), 6.56 (1H, d, 8 Hz), 6.69 (1H, d, 9H), 6.82 (1H, d, t, 8 Hz), 7.07 (1H, t, 9 Hz), 7.11 (1H, d, 8 Hz), 7.92 (1H, dd, 3 and 9 Hz), 8.06 (2H, d, 3 Hz); $^{13}$C-NMR (75 MHz, CDCl$_3$): δ 16.6, 18.9, 26.0, 40.0, 48.0, 102.8, 108.4, 118.2, 118.8, 120.5, 122.3, 123.3, 124.0, 127.6, 138.0, 140.4, 146.6, 159.1.

2-Nitro-5a-phenyl-6,6-dimethyl-5a, 6-dihydro-12H-indolo[2,1-b][1,3]benzooxazine (OX2). A solution of 2 (700 mg, 3.2 mmol) and 2-chloromethyl-4-nitrophenol (709 mg, 3.8 mmol) in MeCN (30 mL) was heated under reflux for 48 h. After cooling down to ambient temperature, the solvent was evaporated under reduced pressure and the residue was dissolved in CH$_2$Cl$_2$ (30 mL). The resulting solution was washed with aqueous KOH (0.2 M, 15 mL) and H$_2$O (15 mL). The organic phase was concentrated under reduced pressure and the residue was purified by column chromatography [SiO$_2$:hexane→CH$_2$Cl$_2$/hexane (1:1 v/v)] to give OX2 (680 mg, 58%) as a white solid. HPLC [analytical, MeCN/H$_2$O (95:5)]: RT=3.6 min, PA=2.1, APP=261.0±1.0 nm; mp=176° C.; FABMS: m/z=372 [M]$^+$; $^1$H-NMR (400 MHz, CDCl$_3$): δ 0.89 (3H, s), 1.60 (3H, s), 4.53 (1H, d, 11 Hz), 4.63 (1H, d, 11 Hz), 6.73 (1H, d, 8 Hz), 6.86-6.94 (2H, m), 7.16-7.19 (2H, m), 7.38-7.42 (3H, m), 7.54-7.65 (2H, m), 7.92-7.94 (2H, m); $^{13}$C-NMR (100 MHz, CDCl$_3$): δ 18.6, 27.9, 41.0, 49.9, 105.5, 109.2, 118.3, 120.3, 121.0, 122.6, 123.3, 123.9, 127.9, 128.2, 128.8, 129.1, 136.1, 137.9, 141.4, 147.0, 159.3.

Steady-Sate Absorption Spectroscopy. The absorption spectra were recorded either in aerated MeCN, using quartz cells with a path length of 0.5 cm, or in polymethylmethacrylate (PMMA) matrices. The polymer films were prepared by spin-coating aliquots of CH$_2$Cl$_2$ solutions of PMMA (160 mg mL$^{-1}$) and either OX1 or OX2 (8 mg mL$^{-1}$) with and without Bu$_4$NOH (7 equiv.) on glass plates at 420 rpm for 9 s. The thicknesses of the resulting films was about 6 µm and was measured with a digital micrometer.

Laser Flash Photolysis. Solutions of oxazine (0.1 mM, 22° C.±2° C.) in MeCN were illuminated with the third harmonic of a Nd-YAG Continuum Surelite II-10 laser (355 nm, 6 ns, 6 mJ), using quartz cells with a path length of 1.0 cm. The excited solutions were analyzed with a Luzchem Research mLFP-111 apparatus with an orthogonal pump/probe configuration. The probe source was a ceramic xenon lamp coupled to quartz fiber-optical cables. The laser pulse and the mLFP-111 system were synchronized by a Tektronix TDS 3032 digitizer, operating in pre-trigger mode. The signals from a compact Hamamatsu photomultiplier were initially captured by the digitizer and then transferred to a personal computer, controlled by Luzchem Research software operating in the National Instruments LabView 5.1 environment. The energy of the laser pulse was measured at each shot with a SPHD25 Scientech pyroelectric meter.

Determination of the Quantum Yield for the Transformation of Oxazine into Indolium. The quantum yield ($\Phi_{IN}$) for the photoinduced conversion of oxazine into indolium was determined with equation (1), using an optically-matched MeCN solution of benzophenone as standard. The quantum yield ($\Phi_{BE}$) for the intersystem crossing of benzophenone is unity and the molar extinction coefficient ($\epsilon_{BE}$) for its triplet absorption at 520 nm is 6.5 mM$^{-1}$ cm$^{-1}$. The molar extinction coefficient ($\epsilon_{IN}$) of indolium at 440 nm was estimated to be about 22 mM$^{-1}$ cm$^{-1}$ from the absorption spectrum of potassium p-nitrophenolate. The terms $\chi_{IN}$ and $\chi_{BE}$ in equation (1) are the slopes of the linear portions of plots of the photoinduced absorbance changes, measured at the end of the pulse for indolium and the benzophenone triplet respectively, against the energy of the laser pulse.

$$\Phi_{IN} = \frac{\chi_{IN} \varepsilon_{BE} \Phi_{BE}}{\chi_{BE} \varepsilon_{IN}} \quad (1)$$

Determination of the Quantum Yield of Singlet Oxygen. The evolution of singlet oxygen ($^1\Delta_g$) in the course of the photoinduced transformation of oxazine into indolium was monitored by luminescence measurements in air-saturated MeCN. Upon laser excitation of oxazine, the emission of singlet oxygen at 1.27 µµm was probed orthogonally to the exciting beam with a pre-amplified (low impedance) Ge-photodiode (Hamamatsu El-P, 300 ns resolution) maintained at −196° C. and coupled to a long-pass silicon filter (>1.1 µm) and an interference filter (1.27 µm). The temporal profile of the luminescence was fitted to a single-exponential decay function with the exclusion of the initial portion of the plot, which is affected by the scattered excitation. The luminescence at initial time was extrapolated from the curve fitting. The quantum yield ($\Phi_{\Delta 1}$) of singlet oxygen was determined with equation (2), using an optically-matched and air-saturated MeCN solution of benzophenone as standard. The quantum yield ($\Phi_{\Delta 2}$) of singlet oxygen formed upon excitation of benzophenone is 0.37. The terms $\chi_1$ and $\chi_2$ in equation (2) are the slopes of the linear portions of plots of the singlet-oxygen luminescence, determined at initial time upon excitation of oxazone and benzophenone respectively, against the energy of the laser pulse.

$$\Phi_{\Delta 1} = \frac{\chi_1 \Phi_{\Delta 2}}{\chi_2} \quad (2)$$

Some of the above results are disclosed in Tomasulo et al. (Org. Lett. 7:1109-1112, 2005), Tomasulo et al. (J. Org. Chem. 70: 8180-8189, 2005), and associated supporting information; all of which are also incorporated by reference herein in their entirety.

Six additional compounds have been synthesized. Compounds 9 and 13-14 were synthesized in accordance with the above. Compounds 10-12 were synthesized by displacing a methyl at $R^4$ by aldehyde condensation. The conjugated systems at $R^1$ and $R^4$ are expected to shift absorbance ($\lambda_{max}$) to longer wavelengths.

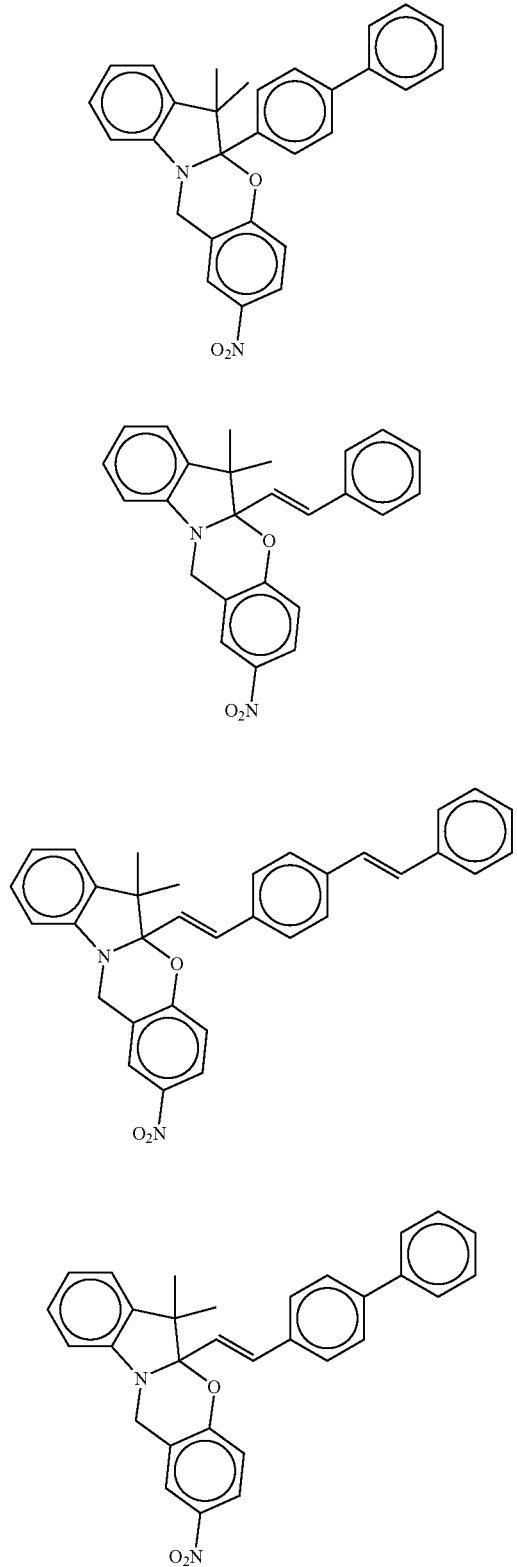

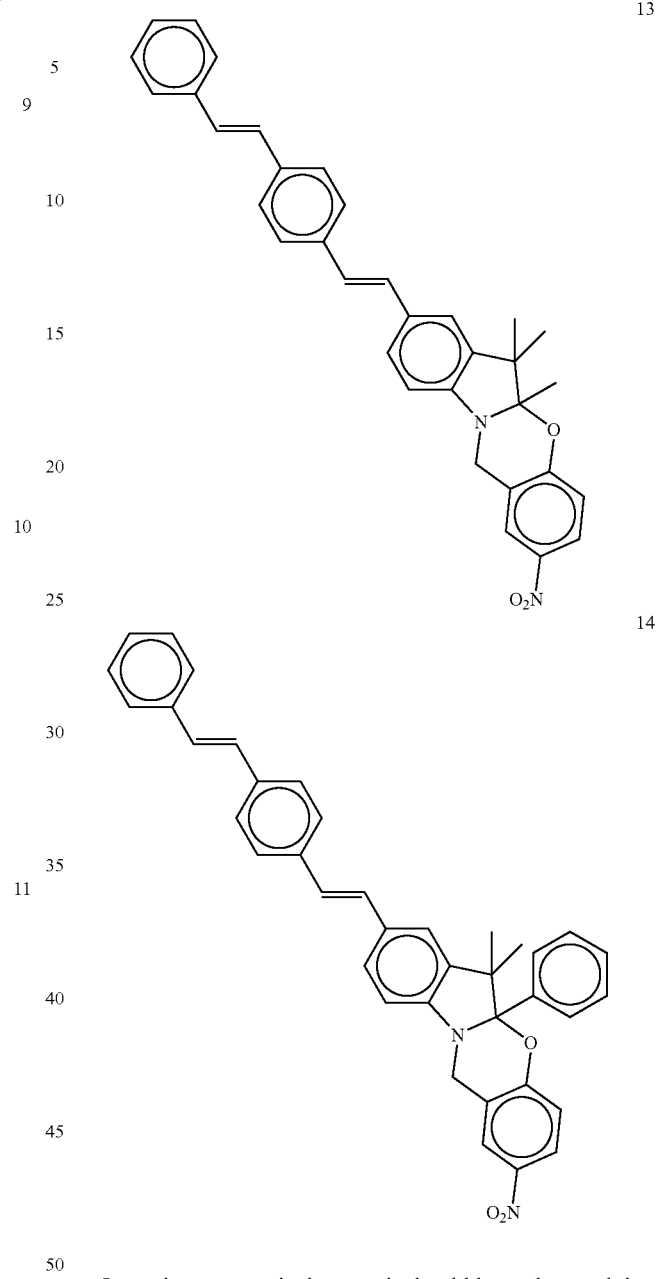

In stating a numerical range, it should be understood that all values within the range are also described (e.g., one to ten also includes every integer value between one and ten as well as all intermediate ranges such as two to ten, one to five, and three to eight).

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

We claim:

1. A photochromic compound which is a [1,3]oxazine compound substituted at one or more positions, wherein the unsubstituted [1,3]oxazine compound is described as having a structure with fused indoline and benzooxazine fragments such that they are fused along (i) the bond connecting positions 1 and 2 of the indoline fragment and (ii) the bond connecting positions 2 and 3 of the benzooxazine fragment, and further substituted by an electron withdrawing group for a hydrogen attached at any position of the phenyl ring of the benzooxazine fragment, wherein said [1,3]oxazine compound has a substituted structure as shown in Formula I:

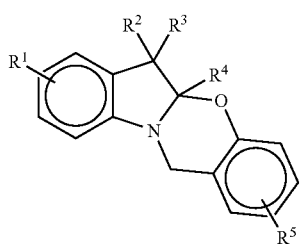

Formula I wherein $R^1$, $R^4$, and $R^5$ are selected to adjust (i) excitation wavelength for cleavage of the [C—O] bond in said compound to produce a phenolate derivative by the ring cleavage and (ii) absorbance wavelength of the phenolate derivative and $R^2$ and $R^3$ are selected to adjust the [1,3]oxazine compound's rate of coloration and/or decoloration, wherein said $R^2$ and $R^3$ are different;

wherein said $R^1$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles;

wherein said $R^2$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles;

wherein said $R^3$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles;

wherein said $R^4$ is selected from the group consisting of hydrogen, hydroxyl, C1-C4 alkyls, C5-C6 cycloalkyls, substituted C1-C4 alkyls, substituted C5-C6 cycloalkyls, C5-C6 aryls, substituted C5-C6 aryls, C5-C6 heterocycles, and substituted C5-C6 heterocycles;

wherein said $R^5$ is a nitrogen-containing group or any other electron withdrawing substituent;

wherein a light excitation induces cleavage of a [C—O] bond in the oxazine ring of said compound to produce a phenolate derivative by ring cleavage;

wherein said compound switches to said phenolate derivative in 250 ns or less;

wherein isomerization between said compound and said phenolate derivative is thermally reversible without said light.

2. The compound of claim 1, wherein light induces cleavage of a [C—O] bond in the oxazine ring of said compound to produce a phenolate derivative by ring cleavage, wherein said light has a wavelength from 200 nm to 800 nm.

3. The compound of claim 1, wherein light induces cleavage of a [C—O] bond in the oxazine ring of said compound to produce a phenolate derivative by ring cleavage, wherein said light has a wavelength from 800 nm to 1300 nm.

4. A method of making the compound of claim 1, said method comprising N-alkylating 2-$R^4$-3,3'-$R^2$,$R^3$-6—$R^1$-3H-indole with 2-chloromethyl-4-$R^5$-phenol to produce an intermediate and then cyclizing the intermediate under basic conditions.

5. The photochromic compound of claim 1 wherein said compound remain able to isomerizes between said compound and said phenolate derivative over greater than 1000 excitation cycles.

* * * * *